US009801999B2

(12) United States Patent
Okajima et al.

(10) Patent No.: US 9,801,999 B2
(45) Date of Patent: Oct. 31, 2017

(54) MANUFACTURING METHOD OF TWO-CHAMBER TYPE COMBINED CONTAINER-SYRINGE

(71) Applicant: ARTE CORPORATION, Tokyo (JP)

(72) Inventors: Kiyoshi Okajima, Takahagi (JP); Seiji Shimazaki, Takahagi (JP)

(73) Assignee: ARTE CORPORATION, Tokyo (JP)

( * ) Notice: Subject to any disclaimer, the term of this patent is extended or adjusted under 35 U.S.C. 154(b) by 703 days.

(21) Appl. No.: 14/272,500

(22) Filed: May 7, 2014

(65) Prior Publication Data

US 2015/0013276 A1    Jan. 15, 2015

(30) Foreign Application Priority Data

May 8, 2013    (JP) .................................. 2013-098825

(51) Int. Cl.
*A61J 1/20*    (2006.01)
*A61L 2/07*    (2006.01)
(Continued)

(52) U.S. Cl.
CPC .............. *A61M 5/2448* (2013.01); *A61J 1/20* (2013.01); *A61L 2/07* (2013.01); *A61M 5/001* (2013.01);
(Continued)

(58) Field of Classification Search
CPC .......................... A61M 2207/00; B01D 19/00
(Continued)

(56) References Cited

U.S. PATENT DOCUMENTS 1,305,908 A * 6/1919 Lanier .................. B65D 85/321
206/499
4,774,772 A * 10/1988 Vetter .................... A61M 5/008
211/69
(Continued)

FOREIGN PATENT DOCUMENTS

DE    2839219 A1    3/1980
JP    B-04-046152 B    7/1992
(Continued)

OTHER PUBLICATIONS

Extended Search Report for European Patent Application No. 14167423.4 dated Feb. 5, 2015.
(Continued)

*Primary Examiner* — Thanh Truong
*Assistant Examiner* — Patrick Fry
(74) *Attorney, Agent, or Firm* — Nixon Peabody LLP; Jeffrey L. Costellia

(57) ABSTRACT

A manufacturing method of two-chamber type combined container-syringe including: a vacuum plugging process (S2) of eliminating air bubbles from the dissolving solution of the dissolving solution-filled cartridge and sealing the dissolving solution with a middle stopper after the dissolving solution filling process (S1); a vacuum plugging process (S2) has a first cooling processing (S21) of cooling the inside of a vacuum plugging equipment in which a dissolving solution-filled cartridge is disposed to a cooling temperature that does not freeze the dissolving solution, a first decompression processing (S23) of decreasing a pressure inside the vacuum plugging equipment while the vacuum plugging equipment maintains the cooling temperature after the first cooling processing (S21), and a middle stopper pushing processing (S24) of pushing the middle stopper downward and bringing the middle stopper into contact with the dissolving solution after the first decompression processing
(Continued)

(S23). The dissolving solution can be easily filled in a bubble-free state in the two-chamber type combined container-syringe.

10 Claims, 20 Drawing Sheets

(51) Int. Cl.
| | | |
|---|---|---|
| *A61M 5/178* | (2006.01) | |
| *A61M 5/24* | (2006.01) | |
| *A61M 5/28* | (2006.01) | |
| *A61M 5/31* | (2006.01) | |
| *B65B 3/02* | (2006.01) | |
| *B65B 7/16* | (2006.01) | |
| *B65B 7/28* | (2006.01) | |
| *B65B 29/10* | (2006.01) | |
| *B65B 31/02* | (2006.01) | |
| *B65B 63/08* | (2006.01) | |
| *B65B 3/00* | (2006.01) | |
| *A61M 5/00* | (2006.01) | |

(52) U.S. Cl.
CPC .......... *A61M 5/008* (2013.01); *A61M 5/1782* (2013.01); *B65B 3/003* (2013.01); *B65B 3/027* (2013.01); *B65B 7/161* (2013.01); *B65B 7/2821* (2013.01); *B65B 29/10* (2013.01); *B65B 31/027* (2013.01); *B65B 63/08* (2013.01); *A61M 5/002* (2013.01); *A61M 5/284* (2013.01); *A61M 2005/3114* (2013.01); *A61M 2207/00* (2013.01); *B65B 2220/14* (2013.01); *B65B 2230/02* (2013.01)

(58) Field of Classification Search
USPC .......................................... 95/156, 175, 247
See application file for complete search history.

(56) References Cited

U.S. PATENT DOCUMENTS

| | | | |
|---|---|---|---|
| 4,792,329 A | 12/1988 | Schreuder | |
| 4,915,913 A | 4/1990 | Williams et al. | |
| 5,176,884 A * | 1/1993 | Taschner | A61L 2/26 137/468 |
| 8,434,240 B2 * | 5/2013 | Thompson, Jr. | F26B 5/06 34/284 |
| 9,333,147 B2 * | 5/2016 | Schuetz | A61J 1/2093 |
| 2003/0183547 A1 | 10/2003 | Heyman | |
| 2006/0054523 A1 | 3/2006 | Porret et al. | |
| 2007/0169434 A1 | 7/2007 | Kinney et al. | |
| 2009/0081090 A1 | 3/2009 | Dayman et al. | |
| 2012/0118777 A1 * | 5/2012 | Kakiuchi | A61M 5/002 206/366 |
| 2012/0192447 A1 * | 8/2012 | Thompson, Jr. | F26B 5/06 34/287 |
| 2012/0209171 A1 | 8/2012 | Vedrine et al. | |

FOREIGN PATENT DOCUMENTS

| | | | |
|---|---|---|---|
| JP | B-046152 B | 7/1992 | |
| JP | A-2002071534 A | 3/2002 | |
| JP | A-2004-513708 A | 5/2004 | |
| JP | A-2005-233664 A | 9/2005 | |
| JP | B-4638553 B | 2/2011 | |
| JP | B-5081330 B | 11/2012 | |
| WO | 03/094999 A1 | 11/2003 | |
| WO | 2006/058435 A2 | 6/2006 | |
| WO | 2012/019983 A1 | 2/2012 | |
| WO | WO 2012019983 A1 * | 2/2012 | ............ A61J 1/2093 |
| WO | WO 2013/031266 A1 | 3/2013 | |

OTHER PUBLICATIONS

Partial Search Report for European Patent Application No. 14167423.4 dated Oct. 23, 2014.
Office Action in Japanese Patent Application No. 2013-098825 dated Sep. 3, 2013.

* cited by examiner

MANUFACTURING METHOD OF TWO-CHAMBER TYPE COMBINED CONTAINER-SYRINGE

BACKGROUND OF THE INVENTION

Field of the Invention

The present invention relates to a manufacturing method of two-chamber type combined container-syringe.

Priority is claimed on Japanese Patent Application No. 2013-098825, filed on May 8, 2013, the content of which is incorporated herein by reference.

Description of Related Art

A combined container-syringe where a syringe is internally filled with an injection preparation and which is designed so that immediate injection for a patient is allowed by being unpacked from a packaging material when in use has been widely adopted by medical institutions around the world, from the viewpoint of convenience, safety and preventing injection drugs from being misused.

In recent years, a so-called two-chamber type combined container-syringe has been introduced in which a front chamber of one syringe is filled with a powder preparation or a lyophilized preparation and a rear chamber is filled with a dissolving solution, a dispersion medium or a suspending solution, and an injection drug is prepared by dissolving or suspending both of these when in use. Among various types of the two-chamber type combined container-syringe, the type disclosed in Japanese Patent No. 1759157 has been known as the most widely adopted.

In the two-chamber type combined container-syringe, a plastic front assembly is fitted to a distal end portion of a glass cartridge, and a finger grip for finger hooking is fitted to a rear end portion. In addition, a bypass which allows the front chamber and the rear chamber to communicate with each other is molded in an approximately central portion of the cartridge having a cylindrical shape. The powder preparation or the lyophilized preparation filled in the inside of the front chamber is sealed in air-tight and liquid-tight manners by a front stopper and a middle stopper, and in addition, the dissolving solution to solve or to suspend the powder preparation or the lyophilized preparation filled in the inside of the rear chamber is sealed in the air-tight and liquid-tight manners by the middle stopper and an end stopper, respectively.

When injection is performed, the end stopper moves forward by pushing a plunger rod, which screws a female screw provided in a rear portion of the end stopper to a male screw in a distal end, toward the front of the syringe. Accordingly, the middle stopper inserted in the anterior end of the rear chamber moves forward together with the dissolving solution filled inside the rear chamber. When the middle stopper reaches a bypass portion molded in a cartridge, the seal is released by the bypass, and thus the dissolving solution flows into the front chamber through the bypass. At a stage when the entire solution in the rear chamber flows into the front chamber and when the distal end of the middle stopper is further pushed by the end stopper passes through the bypass portion, the pushing of the plunger rod is stopped. By properly shaking the entire syringe and by sufficiently dissolving (suspending) the powder preparation and the lyophilized preparation with the dissolving solution, the injection drug is prepared. By pushing the plunger rod, the front stopper is inserted into a bypass chamber provided in the inner portion of a hub luer-lock. By a longitudinal groove on an inner wall of the bypass chamber, a medicinal solution inside the syringe is introduced into an injection needle from an outlet hole of a cylindrical tip. Then, air bubbles remaining inside the front chamber are discharged by further pushing the plunger rod, and thus the injection drug is introduced to the injection needle through the cylindrical tip of the hub luer-lock and injected to a patient.

In this type of the two-chamber type combined container-syringe, a solution, such as the dissolving solution is filled and sealed in the rear chamber, in a state where a glass cartridge is a single body before fitting the front assembly and the finger grip to both ends of the glass cartridge and steam sterilization is performed, and then the lyophilization solution is filled and lyophilized or powder preparation is filled and sealed in the front chamber, and after that, the front assembly or the finger grip can be aseptically fitted. For this reason, the use of this type of two-chamber type combined container-syringe as a combined container-syringe for various kinds of injection drug has been planned and developed.

Technology disclosed in Japanese Patent No. 5081330 and Japanese Patent No. 4638553 have been known as a method of filling and sealing the glass cartridge of this type of two-chamber type combined container-syringe with the medicinal solution. In the disclosed technology, after attaching a plastic holder to the single body of the glass cartridge of the above-described two-chamber type combined container-syringe and putting a plurality of the glass cartridges attached with plastic holders to a plastic nest, it is possible to sterilize by putting the entire body into a tub (container) and covering an upper surface of the tub with a non-woven fabric or a synthetic paper that is sterilizable and by heat sealing the periphery thereof. In this manner, it is possible to attach the holder to the glass cartridge which is washed in advance, and of which an inner surface is coated by a lubricant such as silicone oil and dried, to insert the plurality of the glass cartridges to through-holes of the nest, to put into the tub whose upper surface is heat sealed with the non-woven fabric or the synthetic paper, and to sterilize with high pressure steam or ethylene oxide gas (EOG).

According to such technologies disclosed in Japanese Patent No. 5081330 and Japanese Patent No. 4638553, first, the packaged and sterilized glass cartridges which are put into the tub are set in filling equipment together with the tub, a lid member that seals an upper end of an opening portion of the tub is mechanically detached within the equipment, and the glass cartridges in the nest are unpacked from the tub together with the nest. Then, a filling process is performed in which the end stopper is inserted into the glass cartridge supported by the holder and the nest from an upper part thereof, the middle stopper is inserted after filling the glass cartridge with the dissolving solution, and the dissolving solution is sealed inside the glass cartridge. Then, the steam sterilization is performed while the glass cartridge is filled with the dissolving solution.

The filling process is performed in which each glass cartridge is filled with a main preparation lyophilized from the upper part of each glass cartridge by the same type of the filling equipment, the front stopper is inserted on the sterilized dissolving solution, and thus the main preparation is sealed inside the glass cartridge. Then, the glass cartridge filled with the main preparation is loaded and the lyophilization is performed in a freeze dryer while the glass cartridge filled with the main preparation is inserted in the nest. And then, a process of pushing the front stopper that has been raised in a half-plugged state from the inside of the glass cartridge into the glass cartridge is performed by lowering a shelf plate in the freeze dryer.

According to such a manufacturing method of two-chamber type combined container-syringe, the glass cartridge is in a state of being horizontally movable together with the holder in a range of the internal diameter of the through-hole of the nest. For this reason, there are advantages that it is easy to position the glass cartridge and it is possible to perform a plurality of filling the dissolving solution operations by one line along the alignment of the through-holes of the nest at a time. In other words, it is possible to perform a process from filling the glass cartridge with the dissolving solution to completing the lyophilization in one nest without the glass cartridge as a main member being removed or transferred.

SUMMARY OF THE INVENTION

However, the dissolving solution filled into the glass cartridge in the filling process has to be in a bubble-free state. In the related art, the filling equipment which can fill the dissolving solution into the glass cartridge and seal the glass cartridge packaged by the nest and the tub does not have a function to fill the glass cartridge with the dissolving solution in a bubble-free state. Therefore, a certain volume of air (air bubble) definitely remains in the upper portion of the dissolving solution sealed between the middle stopper and the end stopper inside the glass cartridge.

The air (air bubble) is expanded at a time of steam sterilization after filling the dissolving solution into the glass cartridge and pushes the middle stopper and the end stopper. In some cases, the end stopper is pushed outside the glass cartridge and the middle stopper is moved to the position of the bypass.

In addition, there is an autoclaving method that injects a compressed air into a sterilization equipment at the time of steam sterilization and prevents the stoppers from moving, but additional equipment have to be installed. Even when the sterilization after filling is possible according to such a method, there is a concern that the air bubbles expand and move both of the stoppers if some air bubbles remain in the upper portion of the solution because there is a case where the lyophilization is performed after the sterilization and the inside of the freeze dryer reaches a complete vacuum state.

Considering the above-described problem, an object of the present invention is to provide a manufacturing method of two-chamber type combined container-syringe in which a dissolving solution can be easily filled in a bubble-free state.

A manufacturing method of two-chamber type combined container-syringe according to the present invention includes: a dissolving solution filling process of preparing a dissolving solution-filled cartridge by inserting an end stopper into an inner side of a cartridge which extends along an axis line and has a cylindrical shape, filling a dissolving solution onto the end stopper inside the cartridge, and inserting a middle stopper into a bypass portion positioned on an upper part of the dissolving solution in the cartridge so that the bypass portion is in a communication state; and a vacuum plugging process of eliminating air bubbles from the dissolving solution in the dissolving solution-filled cartridge and sealing the dissolving solution with the middle stopper in which the air bubbles are eliminated after the dissolving solution filling process. The vacuum plugging process has: a first cooling processing of cooling the inside of a vacuum plugging equipment in which the dissolving solution-filled cartridge is disposed to a cooling temperature that does not freeze the dissolving solution; a first decompression processing of decreasing pressure inside the vacuum plugging equipment while the vacuum plugging equipment maintains the cooling temperature after the first cooling processing; and a middle stopper pushing processing of pushing the middle stopper downward and bringing the middle stopper into contact with the dissolving solution after the first decompression processing.

According to the manufacturing method of two-chamber type combined container-syringe, the air dissolved in the dissolving solution is released from the dissolving solution by cooling the dissolving solution during the first cooling processing. In other words, since a saturated solubility of the dissolving solution decreases by cooling, accordingly, the air of which the saturated solubility exceeds the saturated solubility of the dissolving solution is released to the outside of the dissolving solution from the liquid surface of the dissolving solution. Then, as the pressure decreases by the first decompression processing, the air dissolved in the inside of the dissolving solution is further released, and the air released from the dissolving solution passes through a bypass portion and is discharged outside of the cartridge. After that, the middle stopper comes into contact with the liquid surface of the dissolving solution during the middle stopper pushing processing, and thus it is possible to fill the solution in a bubble-free state into the space between the middle stopper and the end stopper.

In addition, in the first cooling processing of the manufacturing method of two-chamber type combined container-syringe according to the present invention, it is preferable that the cooling temperature to be 0 to 10 C. In the first decompression processing, it is preferable that the pressure inside the vacuum plugging equipment to be reduced to 5 to 15 mbar.

Accordingly, it is possible to effectively release the air dissolved in the dissolving solution.

In addition, in the manufacturing method of two-chamber type combined container-syringe according to the present invention, it is preferable that the vacuum plugging process further have an index temperature measurement processing of measuring the temperature of the dissolving solution in a cooling index cartridge with the same configuration as the dissolving solution-filled cartridge which is disposed in the vacuum plugging equipment and formed by the dissolving solution filling process. Furthermore, it is preferable that the first decompression processing to be performed when the temperature of the dissolving solution in the cooling index cartridge becomes the cooling temperature after the first cooling processing.

In the related art, it is difficult to directly measure the temperature of the dissolving solution in the dissolving solution-filled cartridge inside the vacuum plugging equipment, while ensuring sterility of the dissolving solution, and to determine whether or not the temperature of the dissolving solution reaches the cooling temperature.

In contrast, in the present invention, since the cooling index cartridge which has the same configuration as the dissolving solution-filled cartridge in the vacuum plugging equipment is provided, it is possible to estimate the temperature of the dissolving solution in the dissolving solution-filled cartridge by measuring the temperature of the dissolving solution in the cooling index cartridge.

In other words, in a case where the temperature of the dissolving solution-filled in the cooling index cartridge reaches the cooling temperature, it is possible to determine whether or not the dissolving solution in the dissolving solution-filled cartridge has reached the cooling temperature. Therefore, it is possible to easily confirm the time required for the first cooling processing and avoid wasting time.

The manufacturing method of two-chamber type combined container-syringe according to the present invention further includes a steam sterilization process in order to sterilize the dissolving solution-filled cartridge from outside after the vacuum plugging process.

In the manufacturing method of two-chamber type combined container-syringe according to the present invention, the dissolving solution can be filled in a bubble-free state in the vacuum plugging process. Therefore, it is possible to prevent the end stopper or the middle stopper from moving even when the dissolving solution-filled cartridge is heated in the steam sterilization process.

In addition, the manufacturing method of two-chamber type combined container-syringe according to the present invention further includes: a lyophilization solution filling process of preparing a lyophilization solution-filled cartridge in which the lyophilization solution is sealed together with internal gas by the front stopper and the middle stopper, by filling the lyophilization solution on the middle stopper which is inside the dissolving solution-filled cartridge after the steam sterilization process and by inserting the front stopper above the lyophilization solution in the cartridge; and a lyophilization process of forming a lyophilized preparation from the lyophilization solution after the lyophilization solution filling process. The lyophilization process has: a second cooling processing of cooling the temperature inside the freeze dryer in which the lyophilization solution-filled cartridge is disposed; a second decompression processing of making the front stopper be in a half-plugged state with respect to the cartridge by reducing the pressure inside the freeze dryer to be the pressure lower than that of the internal gas, while the temperature inside the freeze dryer is cooled after the second cooling processing; and a front stopper pushing processing of pushing the front stopper downward after changing the lyophilization solution by being frozen in high vacuum to the lyophilized preparation by a sublimation after the second decompression processing.

According to the manufacturing method of two-chamber type combined container-syringe, as the pressure is reduced after cooling the inside of the freeze dryer in which the lyophilization solution-filled cartridge are aligned, a pressure difference between an atmosphere inside the freeze dryer and the internal gas inside the cartridge is generated. As this pressure difference affects the front stopper, the front stopper moves upward. As a result, the front stopper is in a half-plugged state with respect to the cartridge. Accordingly, since the inside and the outside of the cartridge become a communication state, it is possible to form the lyophilized preparation from the lyophilization solution which is lyophilized in the cooled atmosphere inside the freeze dryer. In addition, after completing the lyophilization, it is possible to retain the lyophilized preparation, which is formed by lyophilizing the lyophilization solution by pushing the front stopper into the cartridge, in a sealed state.

In addition, in the manufacturing method of two-chamber type combined container-syringe according to the present invention, it is preferable that the dissolving solution filling process, the vacuum plugging process, the steam sterilization process, the lyophilization solution filling process, and the lyophilization process to be performed in a state where a plurality of cartridges are horizontally aligned and supported in a nest.

Accordingly, it is possible to fill the plurality of cartridges with the dissolving solution and the lyophilized preparation at the same time.

In addition, in the manufacturing method of two-chamber type combined container-syringe according to the present invention, it is preferable that the vacuum plugging process, the steam sterilization process, and the lyophilization process be performed in a state where the plurality of cartridges are stowed together with the nest inside a steel tub which is formed of stainless steel and an upper part thereof is open with a box shape.

By using a steel tub made of stainless steel, even in the steam sterilization process and the lyophilization process, cooling deformation or decompression deformation does not occur in the tub. For this reason, through a series of processes, the tub can have a function as a tub which retains the cartridge and the nest.

In addition, in the manufacturing method of two-chamber type combined container-syringe according to the present invention, the steam sterilization process is performed in a state where the opening of the steel tub is closed with a lid main body made of stainless steel and with a lid member having a filter that closes a hole portion of the lid main body.

It is possible to sanitarily store the cartridge and the like stowed in the tub by closing the opening of the tub with a lid member. Meanwhile, it is possible to reliably perform the sterilization of the cartridge and the like by the steam reaching the inner portion of the tub through the filter at the time of steam sterilization.

In addition, in the manufacturing method of two-chamber type combined container-syringe according to the present invention, it is preferable that the steam sterilization process be performed in a state where the steel tub is disposed to incline so that an axis line of the cartridge is inclined to a vertical direction.

Accordingly, it is possible to reduce the volume of moisture remaining inside the cartridge by dew condensation after the steam sterilization.

In addition, in the manufacturing method of two-chamber type combined container-syringe according to the present invention, it is preferable that a spacer is provided which abuts both a bottom surface of an inner side of the steel tub and a lower end of the plurality of cartridges.

Accordingly, it is possible to avoid an excessive load applied to the cartridge or the nest by the middle stopper pushing processing or the front stopper pushing processing.

In addition, in the manufacturing method of two-chamber type combined container-syringe according to the present invention, it is preferable that height positions of each upper end of the plurality of cartridges stowed in the steel tub be the same and be positioned higher than the opening edge portion of the steel tub. It is preferable that the front stopper pushing processing performed by making a horizontally extended shelf board abuts the front stopper which is in a half-plugged state with respect to each cartridge from above.

Accordingly, it is possible to effectively perform the front stopper pushing processing in an aseptic condition in the freeze dryer. In addition, it is possible to smoothly perform the front stopper pushing processing without interference between the shelf board and the steel tub since the upper end of the cartridge is provided at a position higher than the opening edge portion of the steel tub.

In addition, it is preferable that the vacuum plugging equipment according to the present invention further includes: a cooling index cartridge that has the same configuration as the dissolving solution-filled cartridge disposed in the vacuum plugging equipment and formed by the dissolving solution filling process; and an index temperature measurement portion that measures the temperature of the dissolving solution in the cooling index cartridge.

DETAILED DESCRIPTION OF THE INVENTION

Hereinafter, two-chamber type combined container-syringe (hereinafter, referred to as combined container-syringe) according to an embodiment of the present invention will be described in detail with reference to drawings. The manufacturing method of two-chamber type combined container-syringe according to the embodiment includes a dissolving solution filling process 51, a vacuum plugging process S2, a steam sterilization process S3, a lyophilization solution filling process S4, a lyophilization process S5 and an assembly process S6.

Figure 1:
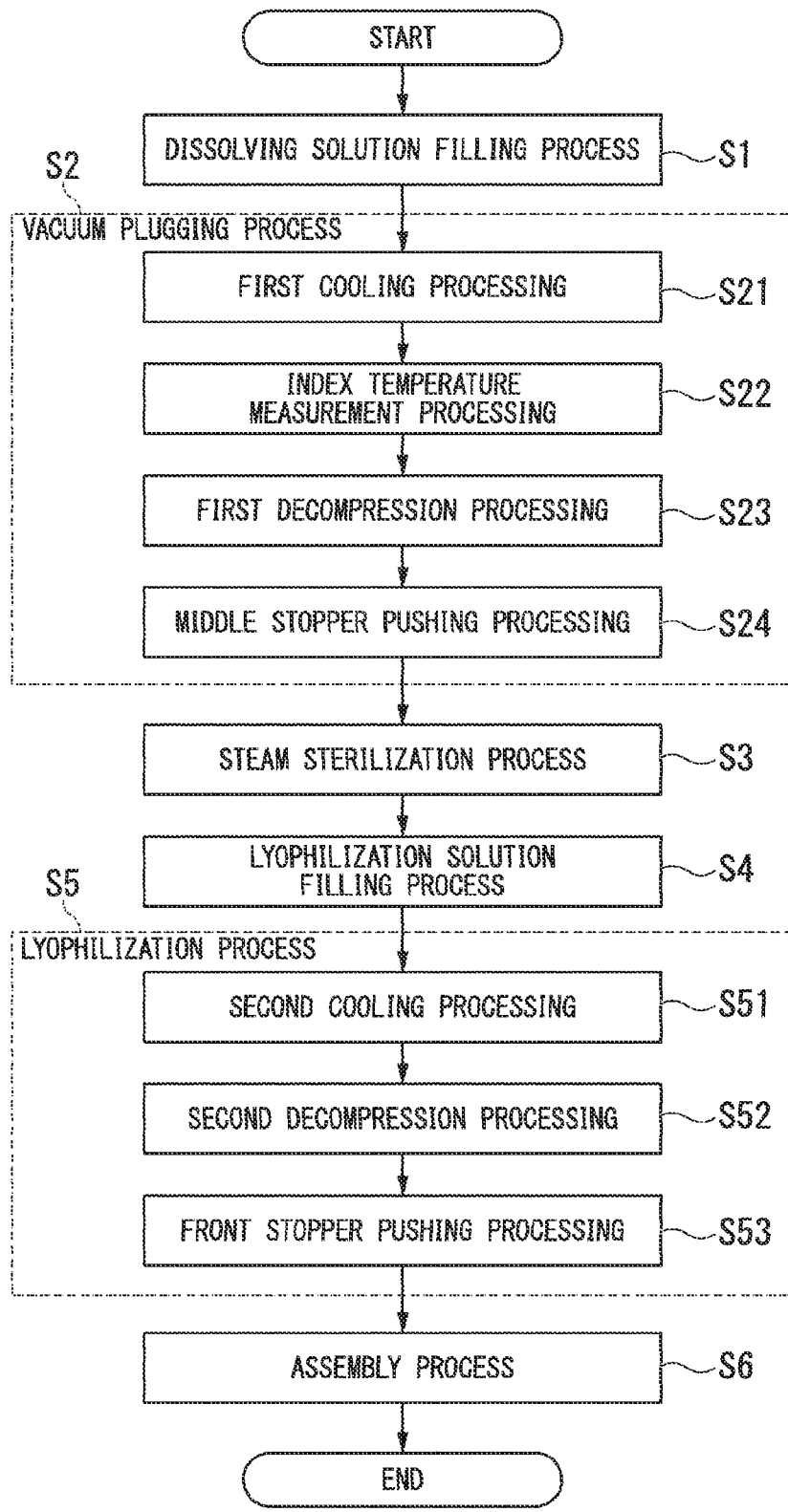
FIG. 1 is a flow chart illustrating an order of a manufacturing method of two-chamber type combined container-syringe according to an embodiment of the present invention.
Figure 2:
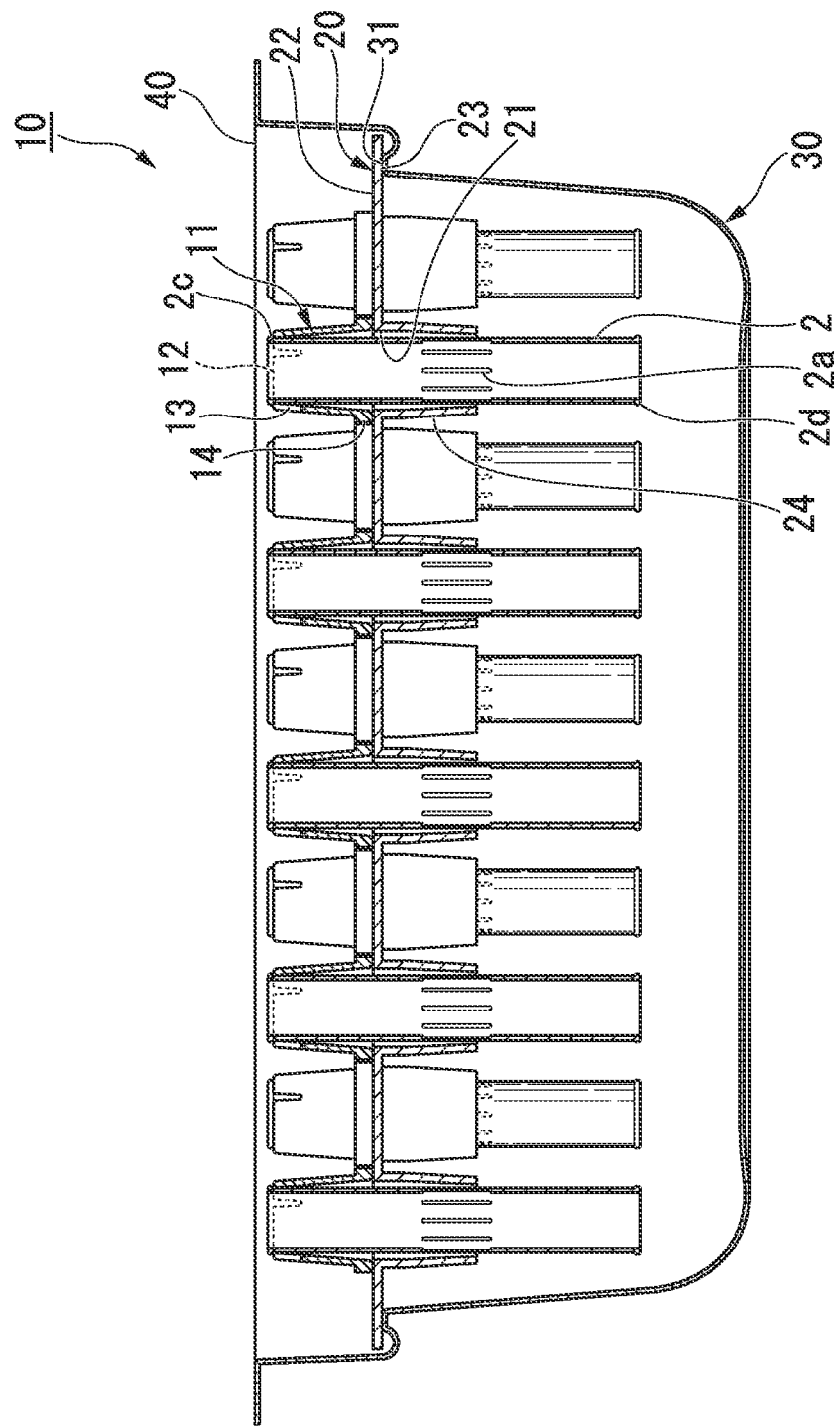
FIG. 2 is a longitudinal sectional view of a cartridge set for preparing a syringe.

The dissolving solution filling process 51 is performed by using a cartridge set for preparing syringe 10 as shown in FIG. 2.

The cartridge set for preparing syringe 10 is provided with a cartridge 2 disposed to be vertically extended, a holder 11, a nest 20, a plastic tub 30, and a synthetic paper filter member 40.

The cartridge 2 has a cylindrical shape that extends along an axis line. At an intermediate part in a direction where the cartridge 2 extends, a bypass portion 2a is provided so that a part of an inner peripheral surface of the cartridge 2 is recessed to the outside in a radial direction and extends in an axial direction of the cartridge 2. Furthermore, an outer peripheral surface of the cartridge 2 has an even outer diameter. In other words, the bypass portion 2a of the embodiment is not protruded from the outer peripheral surface and is a so-called multi-bypass that is formed in a range of a thickness of the cartridge 2.

Furthermore, ringed ribs (distal end side ringed rib 2c, rear end side ringed rib 2d) protruded in a ring shape to the outside in the radial direction from the outer peripheral surface of the cartridge 2 are respectively formed at both ends of the outer peripheral surface of the cartridge 2, that is, opening end portions of the cartridge 2.

The holder 11 is coaxially and externally fitted to the cartridge 2. The holder 11 has a tapered cylindrical shape of which the diameter gradually expands as the holder 11 vertically extends downward from the upper part of the cartridge 2, that is, from the distal end side of the cartridge 2 to the rear end side.

The holder 11 is formed of resin material having flexibility, such as polycarbonate or the like. An internal diameter of an upper end portion 12 of the holder 11 is the same or slightly smaller than the outer diameter of the outer peripheral surface of the cartridge 2. Accordingly, the upper end portion 12 of the holder 11 abuts the outer peripheral surface of the cartridge 2 by the holder 11's own restoring force. In addition, the upper end portion 12 of the holder 11 abuts the distal end side ringed rib 2c of the cartridge 2 that vertically extends, from below.

In this manner, as the holder 11 abuts the cartridge 2 from the outside in the radial direction and from below, the cartridge 2 is supported to be suspended.

In addition, a plurality of slits 13 that extend downward from the upper end portion 12 is formed on the holder 11 in a circumferential direction at intervals. Accordingly, the upper end portion 12 of the holder 11 is formed to easily enlarge the diameter.

Further, a flange portion 14 that protrudes to the outside in the radial direction in a ring shape is formed on a lower end side of the holder 11. An internal diameter of the flange portion 14 is set to be larger than the outer peripheral surface of the cartridge 2, that is, outer diameters of the distal end side ringed rib 2c and the rear end side ringed rib 2d. In addition, a lower surface of the flange portion 14, that is, a lower end surface of the holder 11 is formed in a flat shape that is perpendicular to the axis line of the cartridge 2, and in a ring shape that is centered on the axis line.

The holder 11 is externally fitted to the cartridge 2 from the upper part of the cartridge 2 on which a washing treatment and a silicone treatment are performed. At this time, the diameter of the upper end portion 12 side of the holder 11 is expanded by the distal end side ringed rib 2c, and accordingly, the holder 11 climbs over the distal end side ringed rib 2c. In addition, when the holder 11 is externally fitted to the cartridge 2, it is preferable to apply a force to the flange portion 14 of the holder 11. After that, the upper end portion 12 of the holder 11 is recovered and abuts the outer peripheral surface of the cartridge 2, and at the same time, abuts the distal end side ringed rib 2c from below. Accordingly, without the force applied from outside, the holder 11 is held not to be slipped out from the cartridge 2.

The nest 20 has a board shape that extends along the horizontal plane. A plurality of through-holes 21 that vertically penetrates is arrayed and formed on the nest 20. In the embodiment, the plurality of through-holes is horizontally formed at intervals to be in a zigzag alignment in a plan view. An internal diameter of the through-hole 21 is large enough for the cartridge 2 to be inserted at intervals. In other words, the internal diameter of the through-hole 21 is set to be larger than the outer peripheral surface of the cartridge 2, that is, the outer diameter of the distal end side ringed rib 2c and the rear end side ringed rib 2d. In addition, the internal diameter of the through-hole 21 is set to be smaller than the outer diameter of the lower end surface of the holder 11. In this embodiment, the internal diameter of the through-hole 21 is set to be the same or slightly smaller than the internal diameter of the lower end surface of the holder 11.

A surface facing upward in the nest 20 is parallel to the horizontal plane and has an upper surface for mounting 22 where the lower end surface of the holder 11 is mounted. In addition, a surface facing downward in the nest 20 is parallel to the upper surface for mounting 22, and the outer edge thereof, that is, a region of the entire outer peripheral side is a supported portion 23 that is supported by the plastic tub 30 from below.

Further, in the nest 20, a plurality of sleeves 24 that are formed so that edge portions of each through-hole 21 extend downward in a cylindrical shape is formed to correspond to each through-hole 21. An internal diameter of the sleeve 24 has a tapered shape of which the diameter is gradually reduced downward. The internal diameter at the lower edge is the same or slightly larger than the outer diameter of the rear end side ringed rib 2d of the cartridge 2. Accordingly, when the cartridge 2 is inserted into the through-hole 21, the rear end side ringed rib 2d of the cartridge 2 is made to be able to penetrate the lower end of the sleeve 24. In addition, an internal diameter of an upper end of the sleeve 24 is set to be the same as the internal diameter of the through-hole 21.

The cartridge 2 that is externally fitted to the holder 11 is inserted into each through-hole 21 of the nest 20 downward from above. In a state where the cartridge 2 is inserted into the through-hole 21, the lower end surface of the holder 11 is mounted on the upper surface for mounting 22 of the nest 20. Accordingly, the cartridge 2 is supported by the nest 20 via the holder 11. At this time, the rear end of the cartridge 2 passes through the lower end of the sleeve 24 downward from above and is positioned at a place lower than the lower end of the sleeve 24.

The nest 20 may adopt any material if the material is plastic and has a thermal resistance and a cold resistance, such as polycarbonate, so that the material is not damaged or deformed even when the material is exposed to a severe environment, for example, when the steam sterilization is performed at a temperature about 120 C in a state where 50 to 100 cartridges 2 are suspended, or when the lyophilization is performed at an extremely low temperature. Otherwise, the through-holes 21 that have the same number as the plastic nest 20 may be penetrated on a thin metal plate made of stainless steel or the like. In this case, each of these through-holes 21 is slightly larger than the holes on the plastic plate, and may be fitted to the sleeve 24 molded to have the same internal diameter as the plastic nest 20 so as to be used as a nest 20 for reuse.

The plastic tub 30 has a rectangular box shape that is open upward and is formed of synthetic resin, such as plastic. The diameter of upper portions of four sidewalls of the plastic tub 30 is enlarged by one step toward the outside of the plastic tub 30. Accordingly, a supporting portion 31 which faces upward is formed in a flat plane shape around the entire region of an inner periphery of the plastic tub 30.

In a state where the nest 20 supports the cartridge 2 via the holder 11, the supported portion 23 of the nest 20 abuts the supporting portion 31 from above. Accordingly, in a state where the nest 20 is stowed in the plastic tub 30, the nest 20 is supported by the supporting portion 31.

The synthetic paper filter member 40 is a member that closes the upper portion opening of the plastic tub 30. A non-woven fabric, such as Tyvek, that is welded to the outer periphery of the opening of the plastic tub 30 via a heat sealing or the like can be used as the synthetic paper filter member 40. Accordingly, it is possible to perform sterilization in the plastic tub 30 and the sterility in the inner portion of the plastic tub 30 after sterilization is ensured.

The dissolving solution filling process S1 is performed after sterilizing an outer surface of the cartridge set for preparing syringe 10 and setting the cartridge set for preparing syringe 10 to a filler. The synthetic paper filter member 40 of the cartridge 2 for preparing syringe set in the filler is removed in an isolator. After that, the plurality of cartridges 2 supported by the nest 20 and the holder 11 are removed from the plastic tub 30 together with the nest 20.

Figure 3:
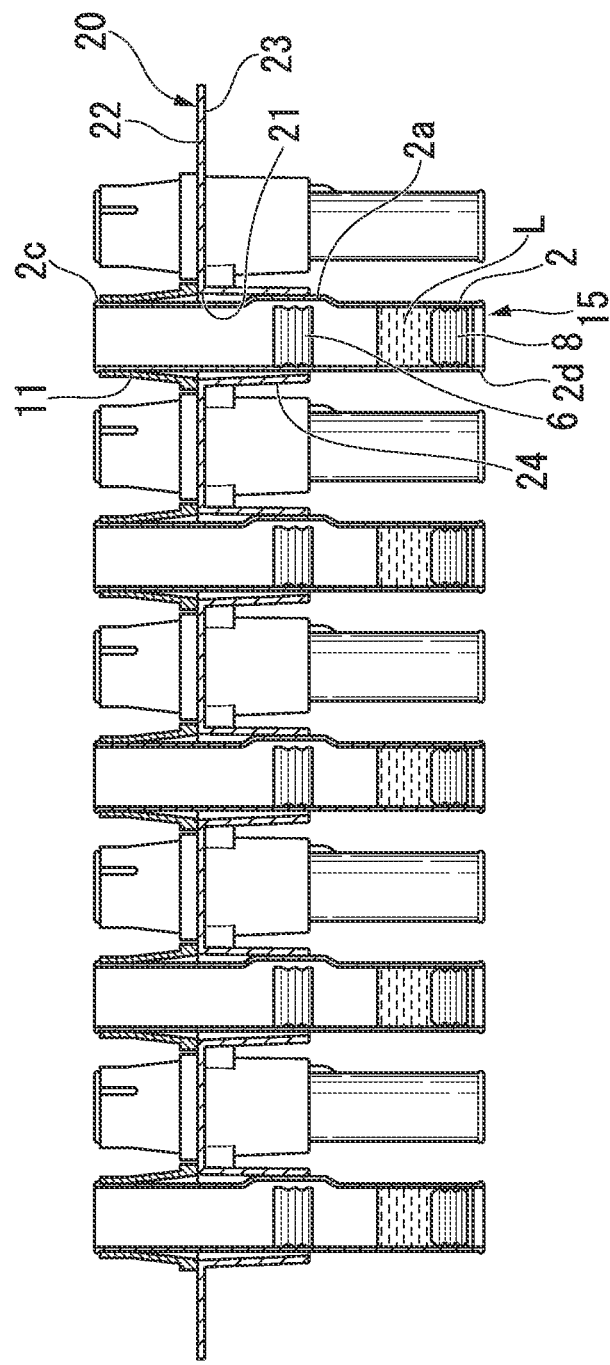
FIG. 3 is a drawing illustrating a dissolving solution filling process.

Then, an end stopper 8 is inserted into the cartridge 2 from above. The end stopper 8 is inserted so as to be positioned at a rear end which is a lower end of the cartridge 2. After that, a dissolving solution L is injected onto the end stopper 8 in the cartridge 2. After that, a middle stopper 6 is inserted to a position of the bypass portion 2a which is an upper portion of the dissolving solution L in the cartridge 2 from the upper end opening of the cartridge 2. Accordingly, a space below and above the middle stopper 6 becomes a communication state via the bypass portion 2a. In this manner, as shown in FIG. 3, a dissolving solution-filled cartridge 15 is formed in which the end stopper 8, the dissolving solution L, and the middle stopper 6 are disposed in the order from the lower side of the cartridge 2 which vertically extends.

Figure 4:
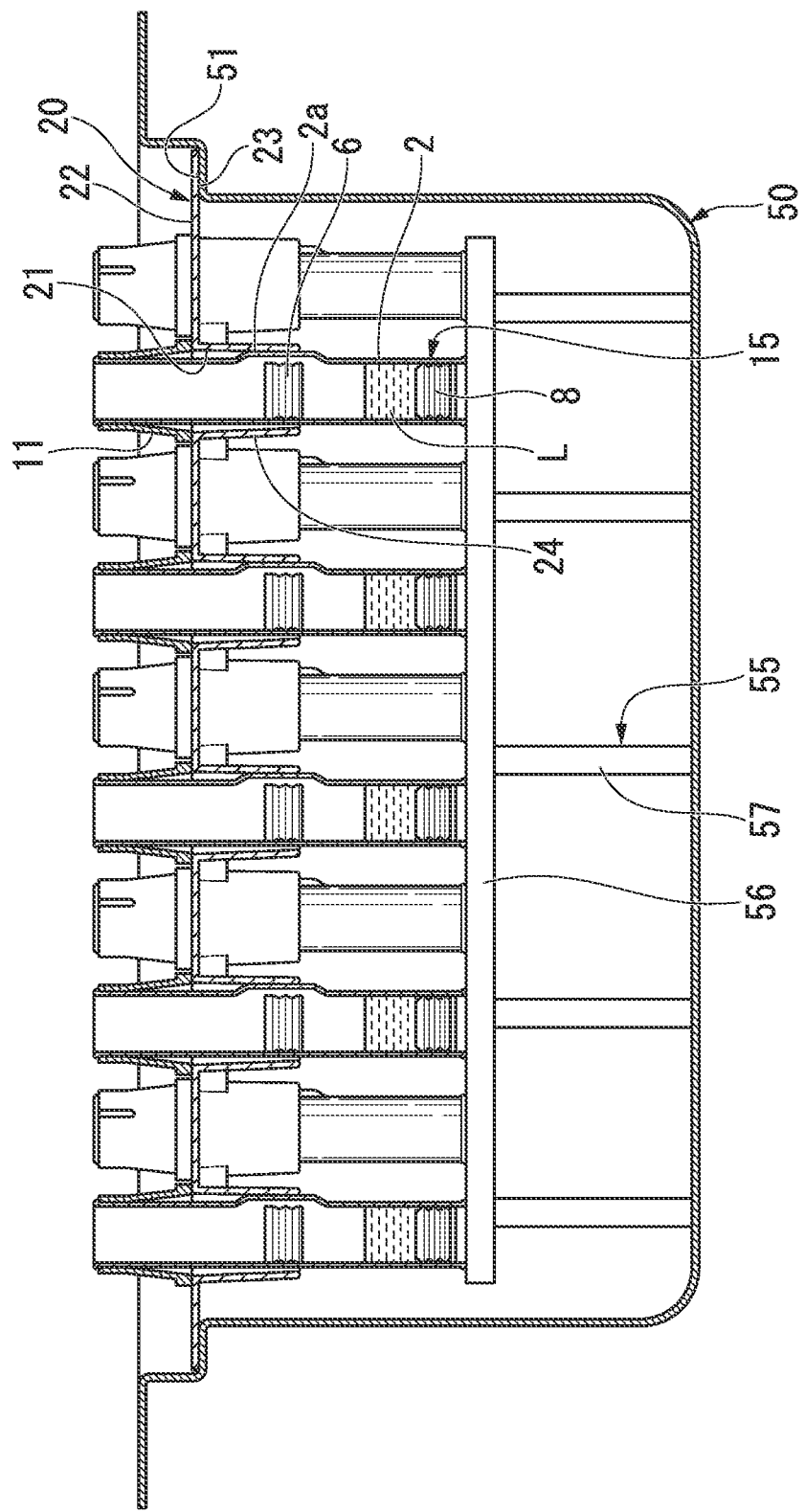
FIG. 4 is a longitudinal sectional view of a steel tub stowing dissolving solution-filled cartridges and a nest.

As shown in FIG. 4, the dissolving solution-filled cartridge 15 is stowed in a steel tub 50 in the filler in a state of being supported by the nest 20.

The steel tub 50 has a rectangular box shape that is open upward and is formed of stainless steel. The diameter of upper portions of four sidewalls of the steel tub 50 is enlarged by one step toward the outside of the steel tub 50. Accordingly, a supporting portion 51 which faces upward is formed in a flat plane shape around the entire region of an inner periphery of the steel tub 50. In a state where the nest 20 supports the dissolving solution-filled cartridge 15 via the holder 11, the supported portion 23 of the nest 20 abuts the supporting portion 51 from above. Accordingly, in a state where the nest 20 is stowed in the steel tub 50, the nest 20 is supported by the supporting portion 51.

The upper ends of the plurality of the dissolving solution-filled cartridges 15 supported by the nest 20, that is, all the upper ends of the cartridges 2 are positioned at the same height and positioned higher than the opening edge portion of the steel tub 50.

The lower ends of the plurality of the dissolving solution-filled cartridges 15 supported by the nest 20, that is, all the lower ends of the cartridges 2 are positioned at the same height. At a space between the lower ends of the cartridges 2 and a bottom portion of an inner side of the steel tub 50, a spacer 55 is provided which abuts both of the lower ends of the cartridges 2 and the bottom portion of an inner side of the steel tub 50.

The spacer 55 is formed of plastic, for example. The spacer 55 has: a board portion 56 which abuts the lower ends of the plurality of cartridges 2 and has a board shape; and a plurality of leg portions 57 which extends downward from the board portion 56 and abuts the bottom portion of the inner side of the steel tub 50.

Figure 5:
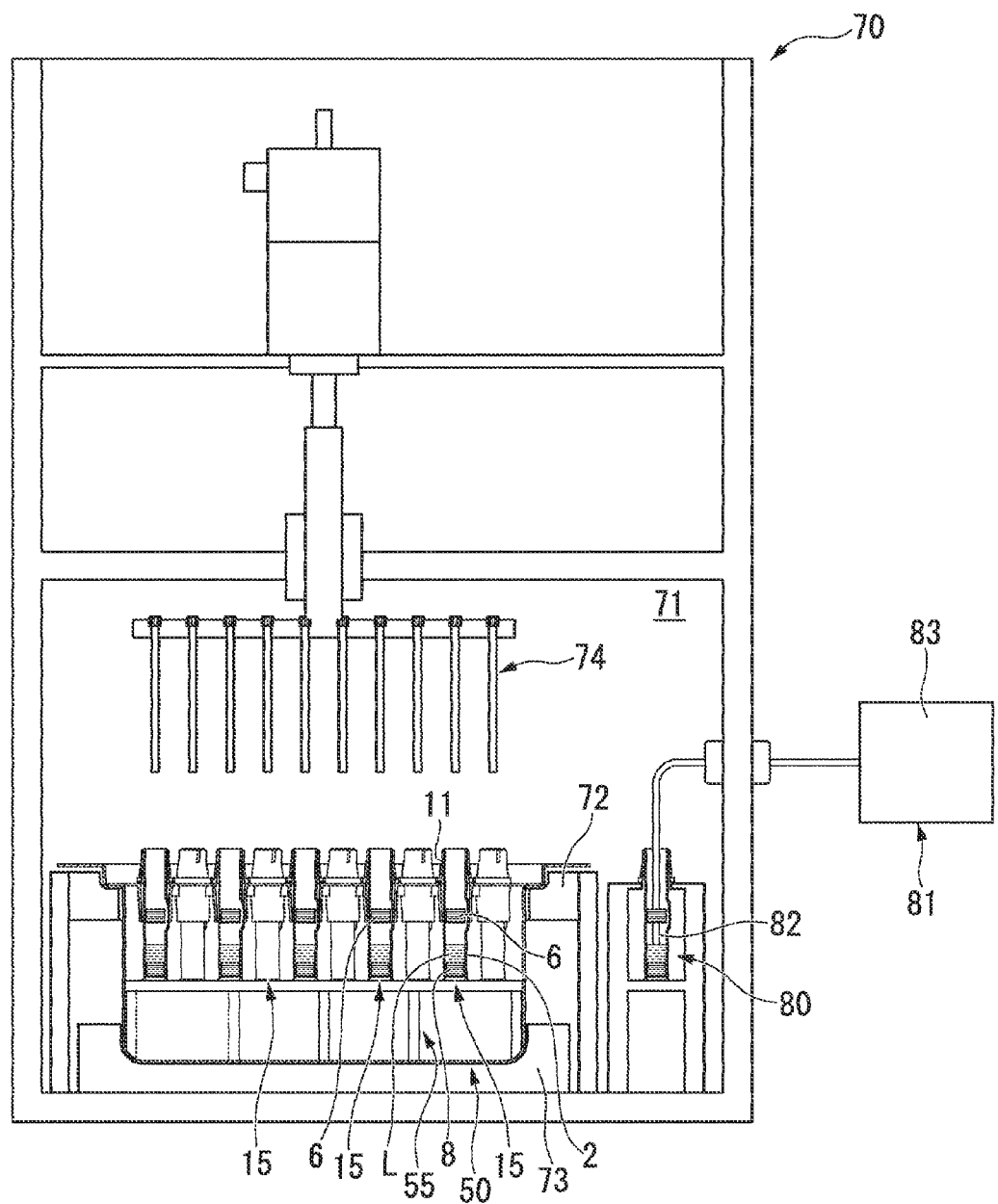
FIG. 5 is a longitudinal sectional view of a vacuum plugging equipment.

Then, the vacuum plugging process S2 is performed. The vacuum plugging process S2 is performed in a vacuum plugging equipment 70 shown in FIG. 5. The vacuum plugging equipment 70 has a chamber 71 in which the steel tub 50 stowing the cartridge 2 and the nest 20 is disposed. In addition, the vacuum plugging equipment 70 has: cooling means (not shown) for cooling the inside of the chamber 71, such as a cooler; decompression means (not shown) for reducing a pressure of an atmosphere of the chamber 71, such as a vacuum pump; and middle stopper pushing means 74. Particularly, the vacuum plugging equipment 70 of the embodiment further has a cooling index cartridge 80 and an index temperature measurement portion 81.

In the chamber 71, a positioning frame 72 that abuts the upper portion side surface of the steel tub 50 and a positioning base 73 that retains the bottom portion of the steel tub 50 are provided. By the positioning frame 72 and the positioning base 73, the steel tub 50 in the chamber 71 is positioned and fixed to be immovable.

Middle stopper pushing means 74 has a plurality of pushing rods corresponding to the upper end openings of the plurality of cartridges 2 stowed in the steel tub 50 fixed in the chamber 71, and has a configuration in which the pushing rods vertically move by oil pressure or air pressure. By descending each pushing rod that is inserted into the inner portions from the upper ends of the cartridges 2, the pushing rods push the middle stoppers 6 downward.

The cooling index cartridge 80 has the same configuration as the dissolving solution-filled cartridge 15. The cooling index cartridge 80 is disposed in the chamber 71, while the steel tub 50 is disposed in the chamber 71. Accordingly, the dissolving solution-filled cartridge 15 stowed in the steel tub 50 and the cooling index cartridge 80 are exposed to the same temperature environment.

The index temperature measurement portion 81 measures the temperature of the dissolving solution L in the cooling index cartridge 80. More specifically, the index temperature measurement portion 81 includes: a thermometer 82 that is inserted into the chamber 71 from the outside of the chamber 71, further passes through the middle stopper 6 of the cooling index cartridge 80, and can measure the temperature of the dissolving solution L; and a monitor 83 that is disposed outside of the chamber 71 and monitors the temperature measured by the thermometer 82.

Hereinafter, the order of the vacuum plugging process S2 will be described. The vacuum plugging process S2 includes a first cooling processing S21, an index temperature measurement processing S22, a first decompression processing S23, and a middle stopper pushing processing S24.

In the vacuum plugging process S2, first, the first cooling processing S21 is performed. As the preparation for the first cooling processing S21, first, the steel tub 50 is set in the chamber 71 of the vacuum plugging equipment 70. In other words, the steel tub 50 stowing the nest 20 and the plurality of the dissolving solution-filled cartridge 15 is set in the state in which that is positioned and fixed in the chamber 71. At the same time, in the chamber 71, the cooling index cartridge 80 is disposed in a similar posture as the dissolving solution-filled cartridge 15 in the steel tub 50. After that, the inside of the chamber 71 becomes a sealed state.

In the first cooling processing S21, the temperature in the chamber 71 is cooled to the cooling temperature that does not freeze the dissolving solution L. It is preferable that the cooling temperature be in a range of 0 to 10 C, for example, and particularly, be more preferable to be set to 5 C. In this manner, the temperature of the dissolving solution L is gradually cooled by cooling the atmosphere in the chamber 71 to the cooling temperature.

In addition, in order to shorten the time to cool the temperature of the dissolving solution L to a predetermined temperature, it is preferable to cool the temperature of the dissolving solution L in a tank in advance before filling and deaerate the chamber 71.

After the first cooling processing S21, the index temperature measurement processing S22 is performed. The index temperature measurement processing S22 is performed in a state where the temperature in the chamber 71 is maintained at a cooling temperature. In the index temperature measurement processing S22, the temperature of the dissolving solution L in the cooling index cartridge 80 is detected via the index temperature measurement portion 81. Accordingly, the temperature of the dissolving solution L in the cooling index cartridge 80 is monitored by the monitor 83 of the index temperature measurement portion 81.

When the temperature of the dissolving solution L measured in the index temperature measurement processing S22 reaches the cooling temperature, the first decompression processing S23 is performed. If the temperature of the dissolving solution L of the cooling index cartridge 80 reaches the cooling temperature, it is estimated that the temperature of the dissolving solution L in the dissolving solution-filled cartridge 15 situated under the similar environment also decreases similarly to the cooling temperature.

In this manner, the dissolving solution L is cooled in the cooling process, and thus the air dissolved in the dissolving solution L is released from the dissolving solution L. In other words, since the saturated solubility of the dissolving solution L decreases by cooling, accordingly, the air of which the saturated solubility exceeds the saturated solubility of the dissolving solution L is released to the outside of the dissolving solution L from the liquid surface of the dissolving solution L.

In the first decompression processing S23, the pressure of the atmosphere in the chamber 71 decreases by decompression means. It is preferable that the pressure in the chamber 71 decrease to 5 to 15 mbar, particularly, to 12 mbar. The first decompression processing S23 is also performed in a state where the cooling temperature is maintained.

According to the first decompression processing S23, the air dissolved in the dissolving solution L is further released, and the air released from the dissolving solution L passes through the bypass portion 2a and is discharged to the outside of the cartridge 2.

Figure 6:
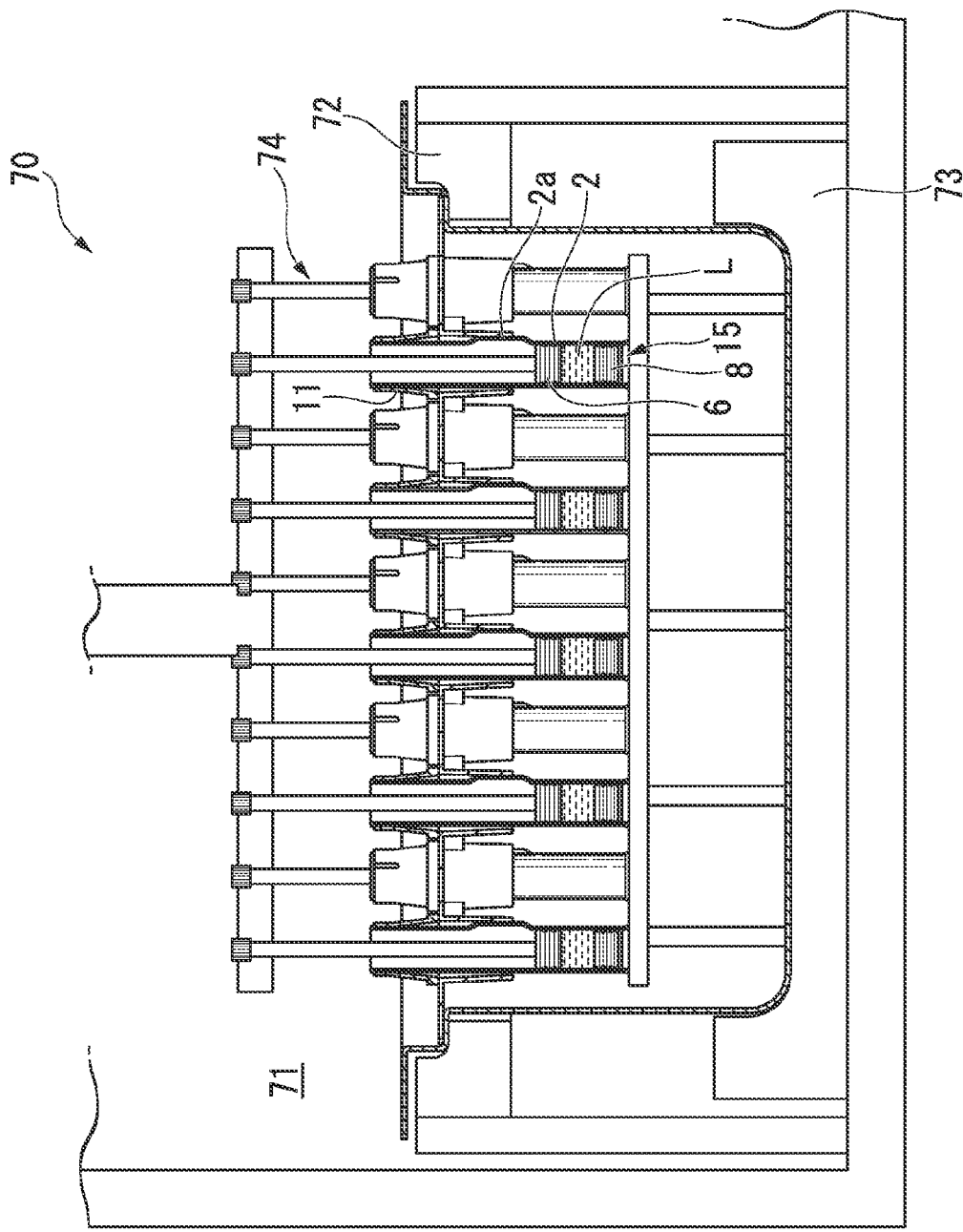
FIG. 6 is a longitudinal sectional view in a state where a middle stopper is pushed in the vacuum plugging equipment.

Then, the middle stopper pushing processing S24 is performed after the first decompression processing S23. In the middle stopper pushing processing S24, as shown in FIG. 6, the middle stopper 6 is moved downward and comes into contact with the liquid surface of the dissolving solution L, and thus it is possible to fill the space between the middle stopper 6 and the end stopper 8 with the dissolving solution L in a bubble-free state. Accordingly, the vacuum plugging process S2 is completed.

In the middle stopper pushing processing S24, a downward load applied to the cartridge 2 via a friction between the pushed middle stopper 6 and the cartridge 2. In the embodiment, since the spacer 55 is interposed between the lower end of the cartridge 2 and the bottom surface of the inner side of the steel tub 50, it is possible to disperse the above-mentioned load via the spacer 55. Accordingly, it is possible to avoid an excessive load being applied to the cartridge 2.

Here, an experiment shows that when the first cooling temperature is 5 C and the pressure is 12 mbar after the decompression in the first decompression processing S23, the middle stopper 6 rarely moves even in the following lyophilization process S5. Therefore, by setting the first cooling temperature to 5 C and the pressure after the decompression in the first decompression processing S23 to 12 mbar, the middle stopper 6 does not move even in the lyophilization process S5 and it is possible to smoothly manufacture the combined container-syringe.

In addition, it is possible to make a bubble-free state because it is possible to effectively remove the gas dissolved in the dissolving solution L by cooling and decompression as described above. It can be presumed that a similar effect can be achieved even when the cooling temperature is 0 to 10 C and the pressure after the decompression is 5 to 15 mbar.

After the vacuum plugging process S2, the steam sterilization process S3 is performed. In the steam sterilization process S3, before starting the process, a lid member 60 is attached to the steel tub 50 unpacked from the chamber 71 of the vacuum plugging equipment 70.

Figure 7:
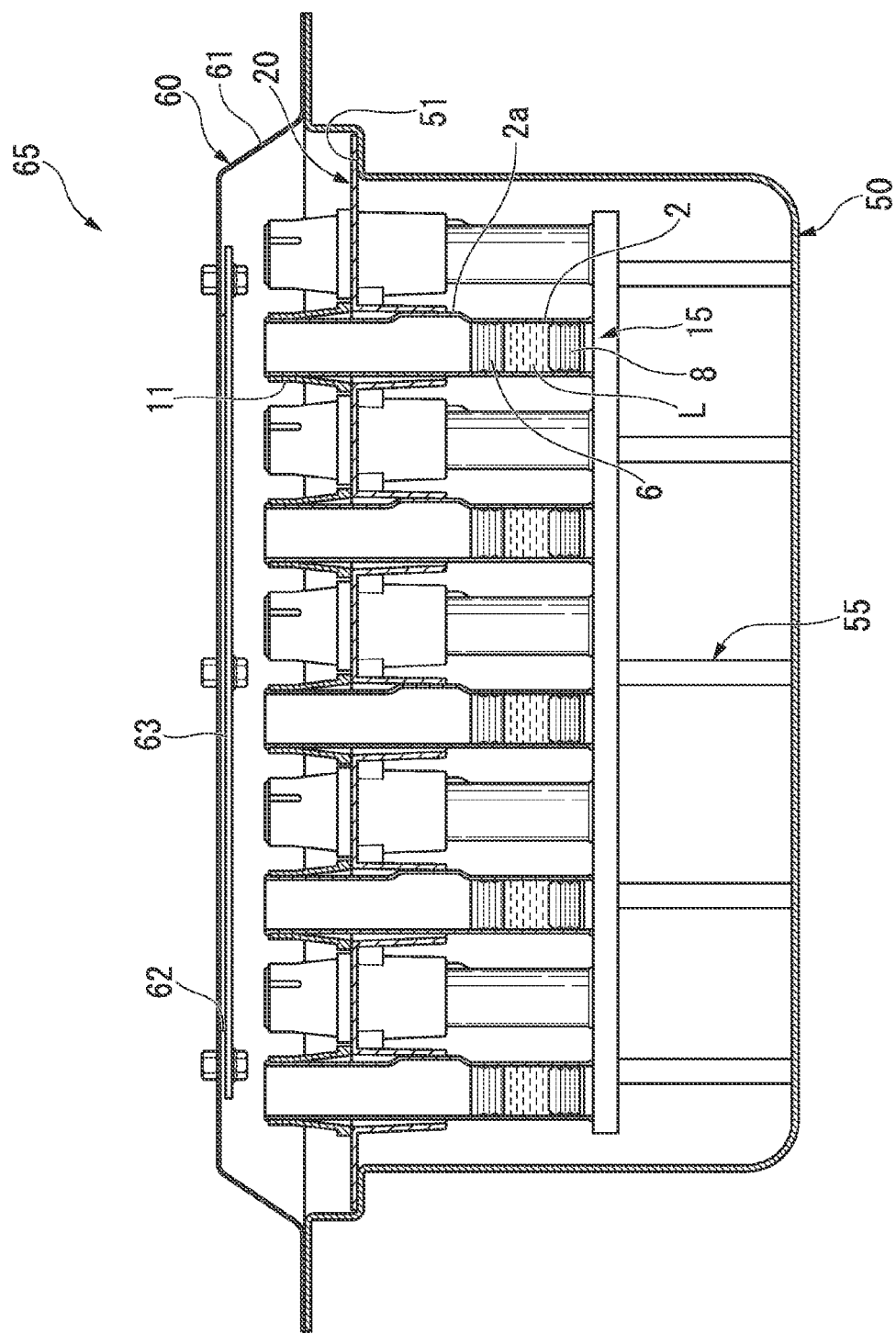
FIG. 7 is a longitudinal sectional view illustrating a state where the dissolving solution-filled cartridge is stowed in a cartridge stowage container made of the steel tub and a lid member.
Figure 8:
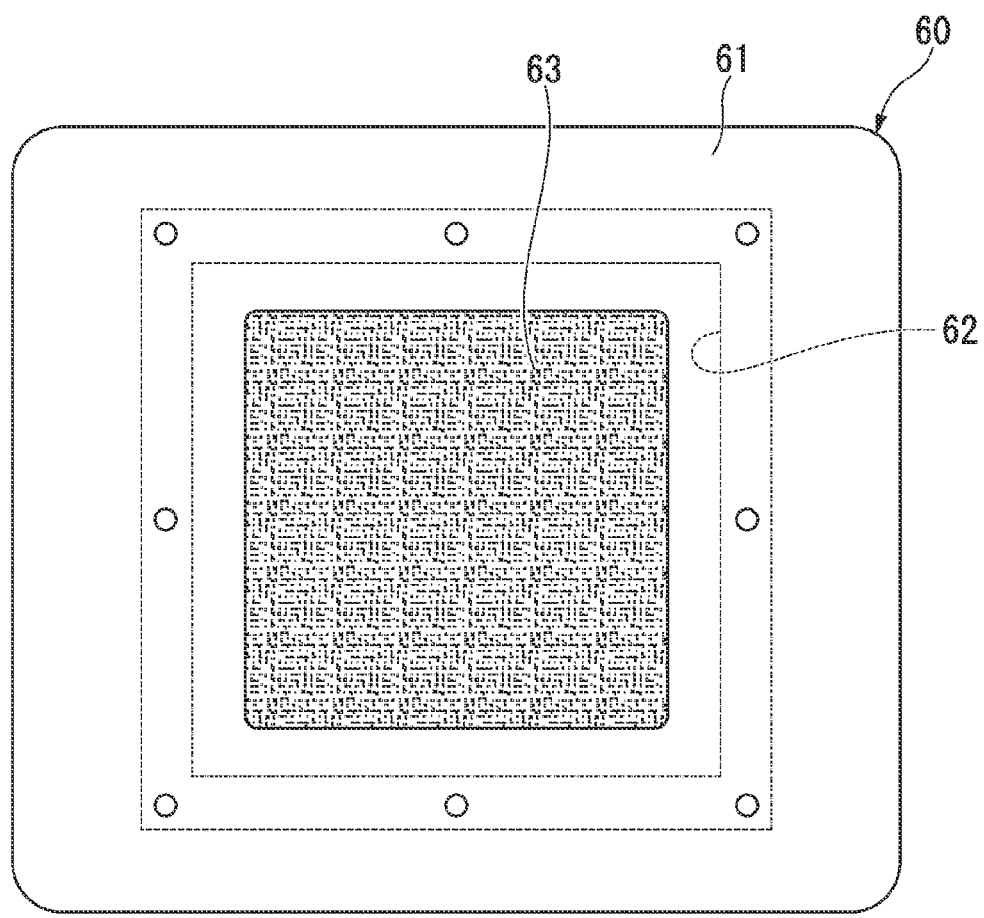
FIG. 8 is a plan view of the lid member.

As shown in FIGS. 7 and 8, the lid member 60 has a lid main body 61 and a filter 63.

The lid main body 61 has a rectangular board shape in a plan view. A hole portion 62 that has a rectangular shape in a plan view is formed in the center portion of the lid main body 61. The filter 63 is a gas-permeable member made of non-woven fabric, synthetic paper, or the like, and is provided to close the hole portion 62 of the lid main body 61.

When an outer peripheral edge portion of the lid main body 61 comes into contact with an outer peripheral edge portion of the opening of the steel tub 50, the lid member 60 is integrated with the steel tub 50. In addition, a seal member, for example, heat-resistant rubber or the like may be interposed at the contact portion between the lid main body 61 and the steel tub 50. In this manner, by the integration of the lid member 60 and the steel tub 50, a cartridge stowage container 65 is configured.

In the steam sterilization process S3, the cartridge stowage container 65 is put into high-pressure steam sterilization equipment and the steam sterilization is performed. Accordingly, the steam with high temperature and high pressure passes through the filter 63, and thus the steam sterilization is performed even to the dissolving solution-filled cartridge 15 and the nest 20 in the cartridge stowage container 65.

Figure 9:
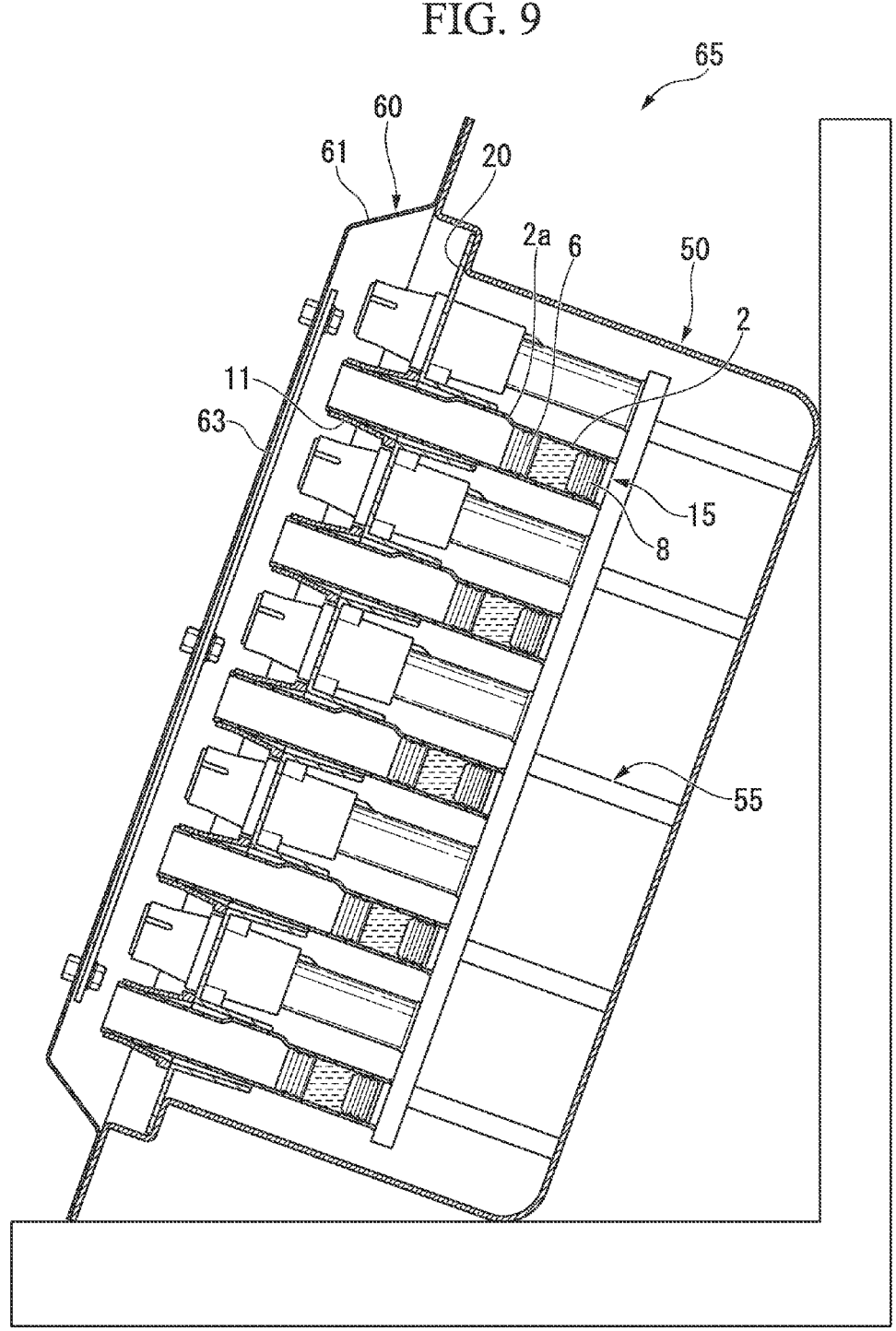
FIG. 9 is a longitudinal sectional view of a state where the cartridge stowage container is inclined.

As shown in FIG. 9, it is preferable to perform the steam sterilization process S3 in a state in which the cartridge stowage container 65 is inclined. Accordingly, it is possible to prevent moisture remaining caused by dew condensation on the middle stopper 6 in the dissolving solution-filled cartridge 15 in the cartridge stowage container 65.

After the steam sterilization process S3, the lyophilization solution filling process S4 is performed.

Figure 10:
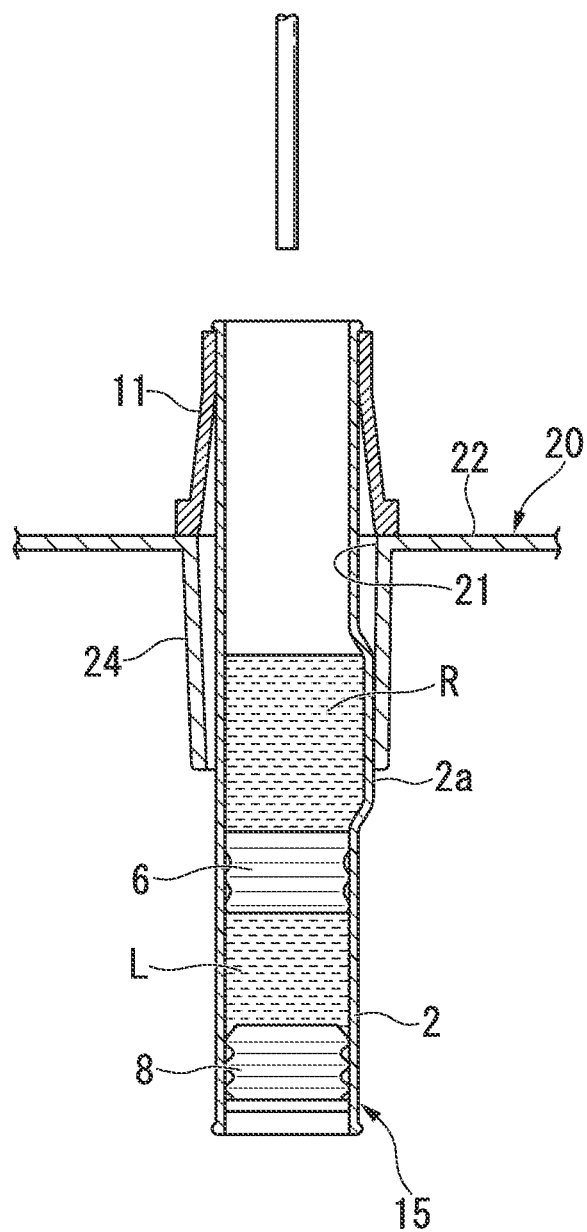
FIG. 10 is a longitudinal sectional view illustrating a state where a lyophilization solution is injected into the cartridge.
Figure 11:
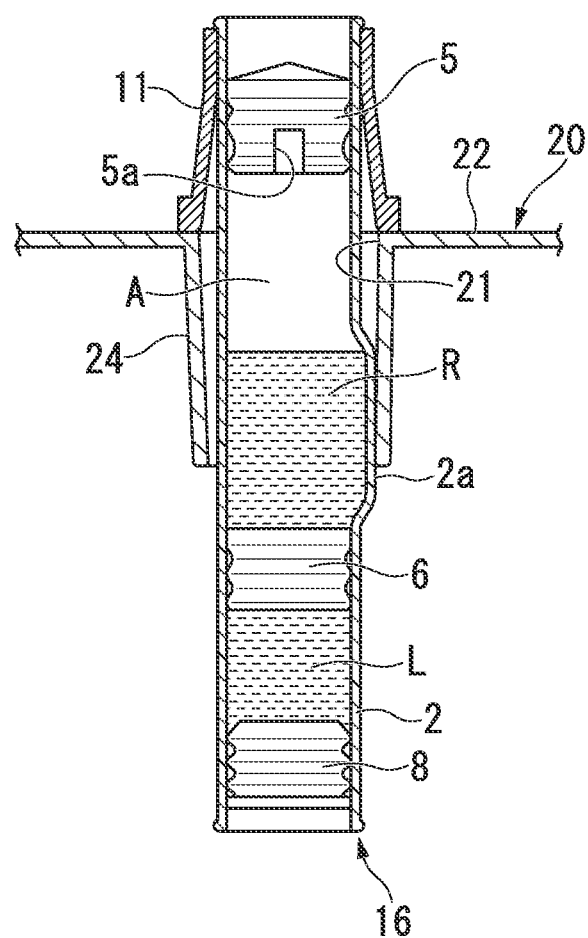
FIG. 11 is a longitudinal sectional view illustrating a state where a front stopper is disposed in the cartridge.

The lyophilization solution filling process S4 is performed in the lyophilization solution filling equipment. In the lyophilization solution filling process S4, first of all, as shown in FIG. 10, a lyophilization solution R is injected onto the middle stopper 6 in the cartridge 2 of the dissolving solution-filled cartridge 15. Then, as shown in FIG. 11, a front stopper 5 is inserted into the upper side of the lyophilization solution R in the cartridge 2. Accordingly, a lyophilization solution-filled cartridge 16 that seals the lyophilization solution R is manufactured by the front stopper 5 and the middle stopper 6 together with an internal gas A.

An air discharging groove 5a is formed in the front stopper 5 by being cut from a surface facing the middle stopper 6 side in the front stopper 5 along the outer peripheral surface. The air discharging groove 5a does not reach the upper end (distal end) of the front stopper 5. Therefore, as shown in FIG. 11, in a state where the front stopper 5 is completely positioned in the cartridge 2, the lower part of the front stopper 5 is in a sealed state.

In the above-described manner, the lyophilization solution filling process S4 is completed. After that, the lyophilization process S5 is performed.

Figure 12:
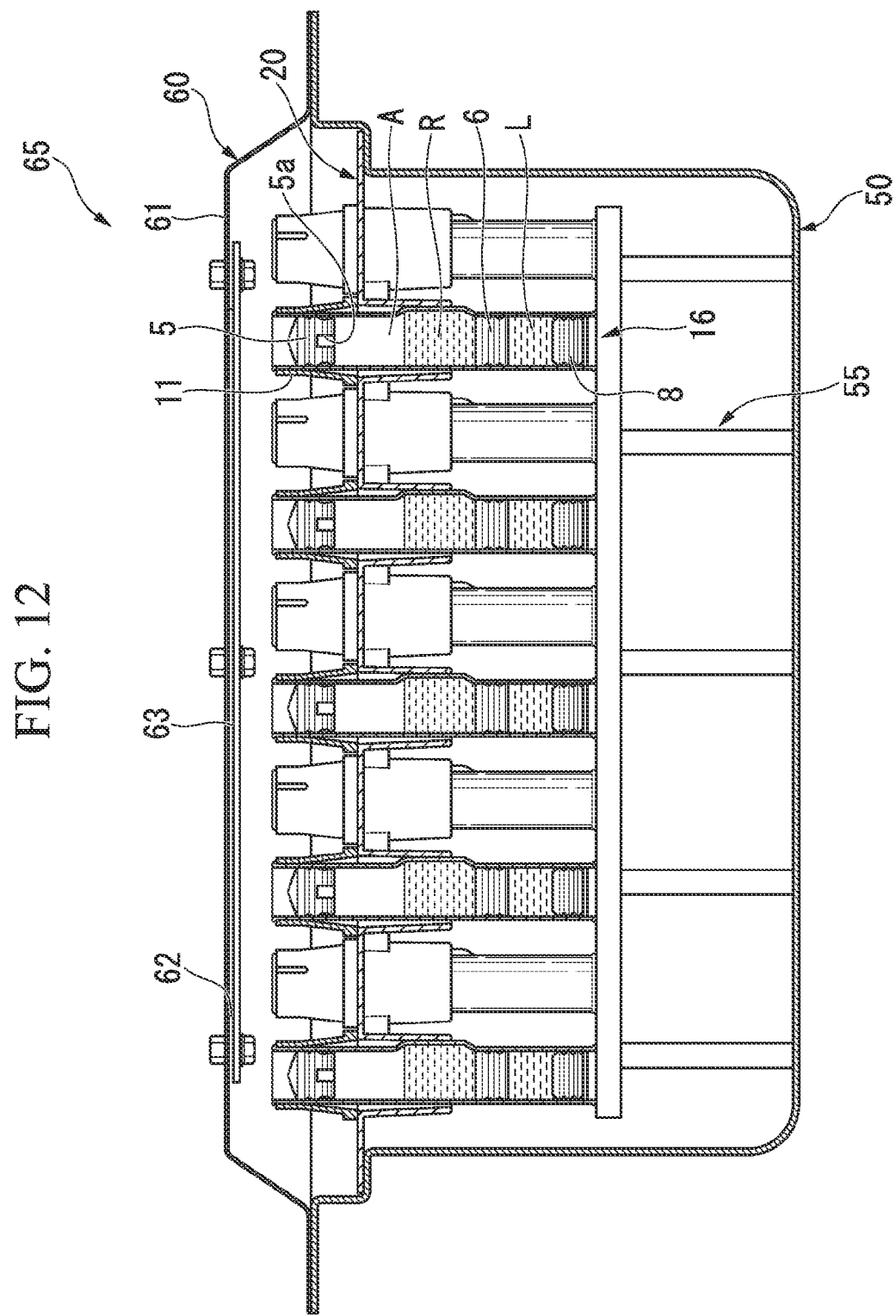
FIG. 12 is a longitudinal sectional view illustrating a state where the lyophilization solution-filled cartridge is stowed in the cartridge stowage container made of the steel tub and the lid member.

Before starting the lyophilization process S5, as shown in FIG. 12, in the lyophilization solution filling equipment, the lid member 60 is reattached to the steel tub 50 that stows the lyophilization solution-filled cartridge 16. After that, the steel tub 50 and the lid member 60 that stows the lyophilization solution-filled cartridge 16, that is, the cartridge stowage container 65 is unpacked from the lyophilization solution filling equipment and is in a standby condition until the number of the cartridge stowage container 65 applied in one lyophilization process S5 is gathered. In addition, even in the standby condition, since the lyophilization solution-filled cartridge 16 is stowed in the cartridge stowage container 65 in an aseptic condition, the sterility is not inhibited.

Figure 13:
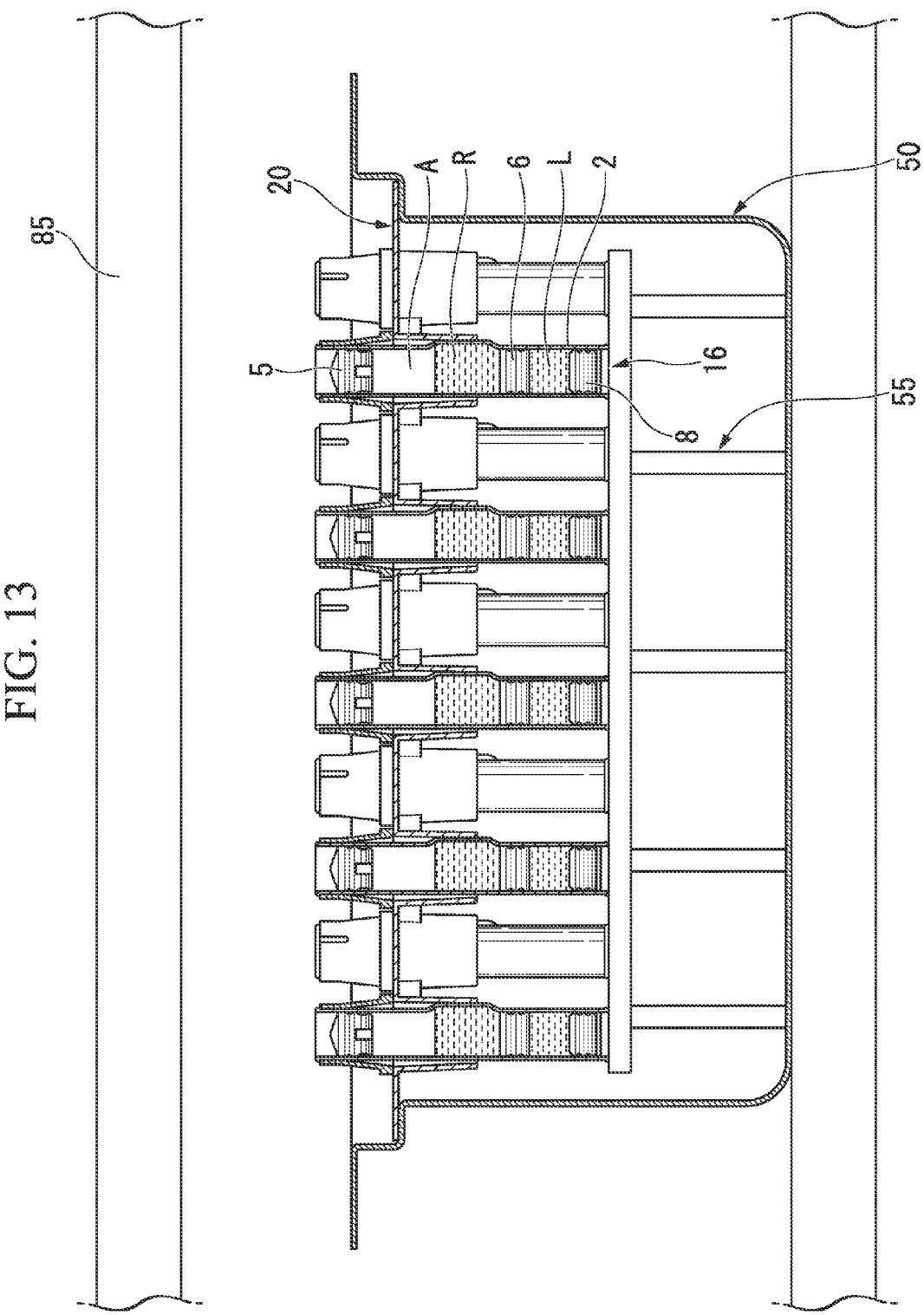
FIG. 13 is a drawing when the steel tub stowing the lyophilization solution-filled cartridge is disposed in the freeze dryer.

After that, as shown in FIG. 13, the cartridge stowage container 65 is set in the freeze dryer after the lid member 60 is removed.

The lyophilization process S5 has a second cooling processing S51, a second decompression processing S52, and a front stopper pushing processing S53.

Figure 14:
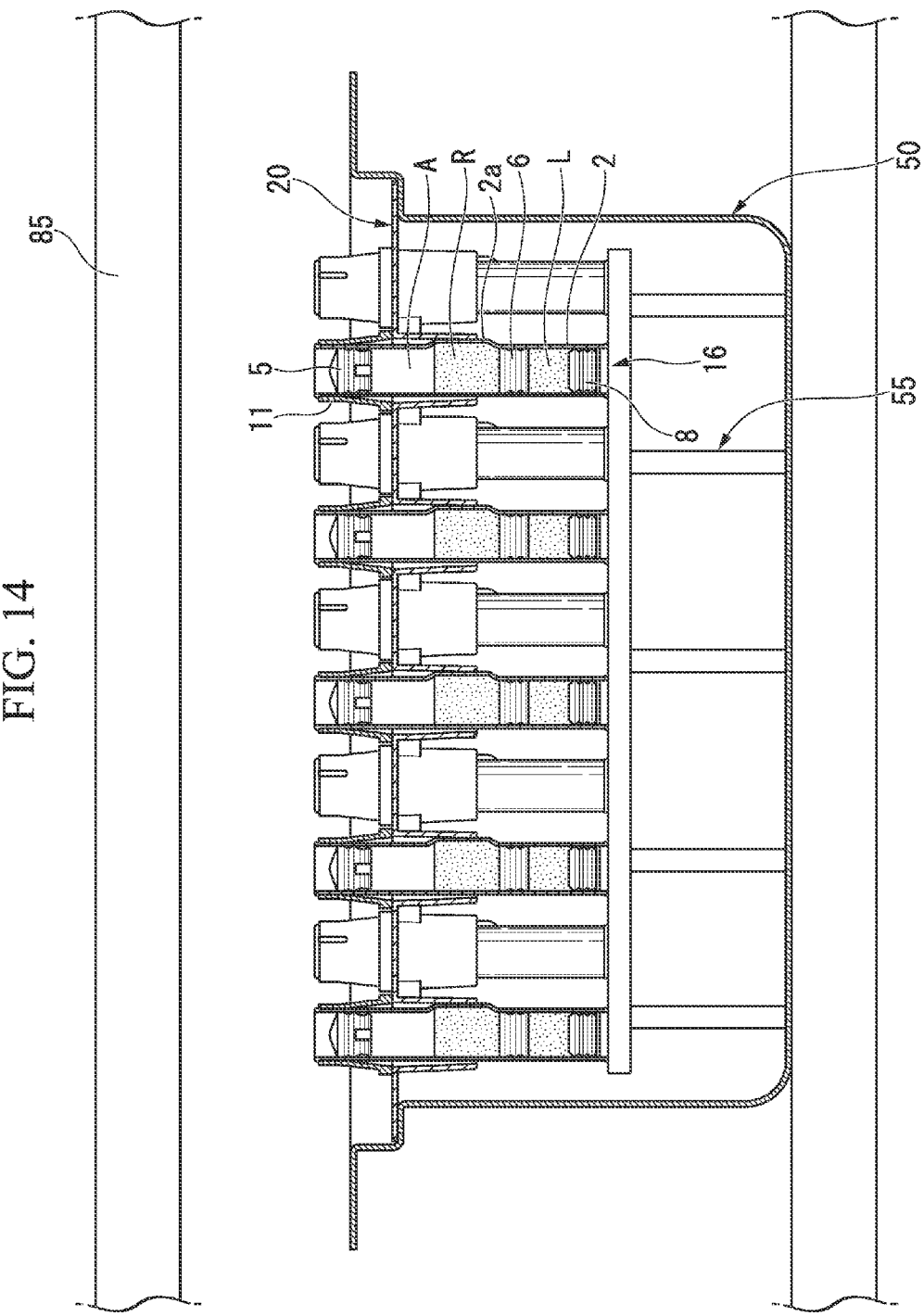
FIG. 14 is a longitudinal sectional view when the steel tub stowing the lyophilization solution-filled cartridge is disposed in the freeze dryer, and a drawing illustrating a state where the inside of the freeze dryer is cooled.

In the second cooling processing S51, the lyophilization solution R is frozen by cooling the temperature in the freeze dryer, that is, by cooling a shelf, on which the lyophilization solution-filled cartridges 16 are disposed on every nest 20 and every steel tub 50, and an outer atmosphere. In addition, it is preferable to cool the temperature of the shelf, on which the lyophilization solution-filled cartridges 16 are disposed, and the outer atmosphere to −40 C to −50 C in the second cooling processing S51. Accordingly, as shown in FIG. 14, the dissolving solution L and the lyophilization solution R in the lyophilization solution-filled cartridge 16 freeze together.

After that, the second decompression processing S52 is performed. The pressure of the atmosphere is reduced by reducing the pressure of the atmosphere in the freeze dryer in the second decompression processing S52. The pressure value of the atmosphere in the initial step becomes sufficiently lower than the pressure of the internal gas A at a space between the middle stopper 6 and the front stopper 5 in the cartridge 2. Accordingly, the pressure difference between the internal gas A and the outer atmosphere affects the front stopper 5 that is inserted into the cartridge 2, and the pressure is applied to the front stopper 5 toward the distal end side (upper side) of the cartridge 2.

Figure 15:
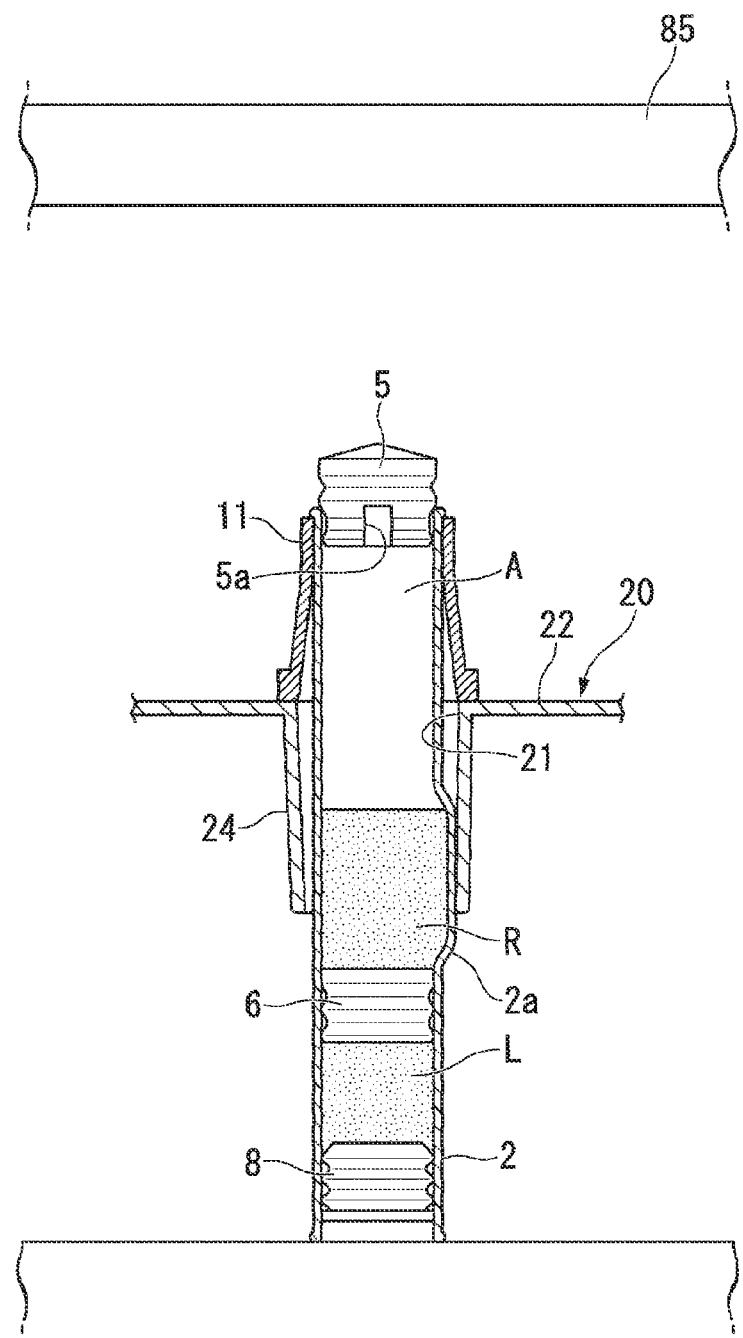
FIG. 15 is a longitudinal sectional view of the cartridge when the front stopper is in a half-plugged state.

As the pressure is applied to the front stopper 5 in this manner, the front stopper 5 moves upward, that is, moves toward the distal end side of the cartridge 2. As shown in FIG. 15, when the front stopper 5 reaches the distal end of the cartridge 2, the front stopper 5 becomes a half-plugged state to the cartridge 2, and thus the pressure inside and outside of the cartridge 2 becomes an equilibrium state. In other words, the inside and the outside of the cartridge 2 becomes a communication state via the air discharging groove 5a in the front stopper 5. Accordingly, since the pressure applied to the front stopper 5 disappears, the movement of the front stopper 5 is stopped at the distal end of the cartridge 2.

Figure 16:
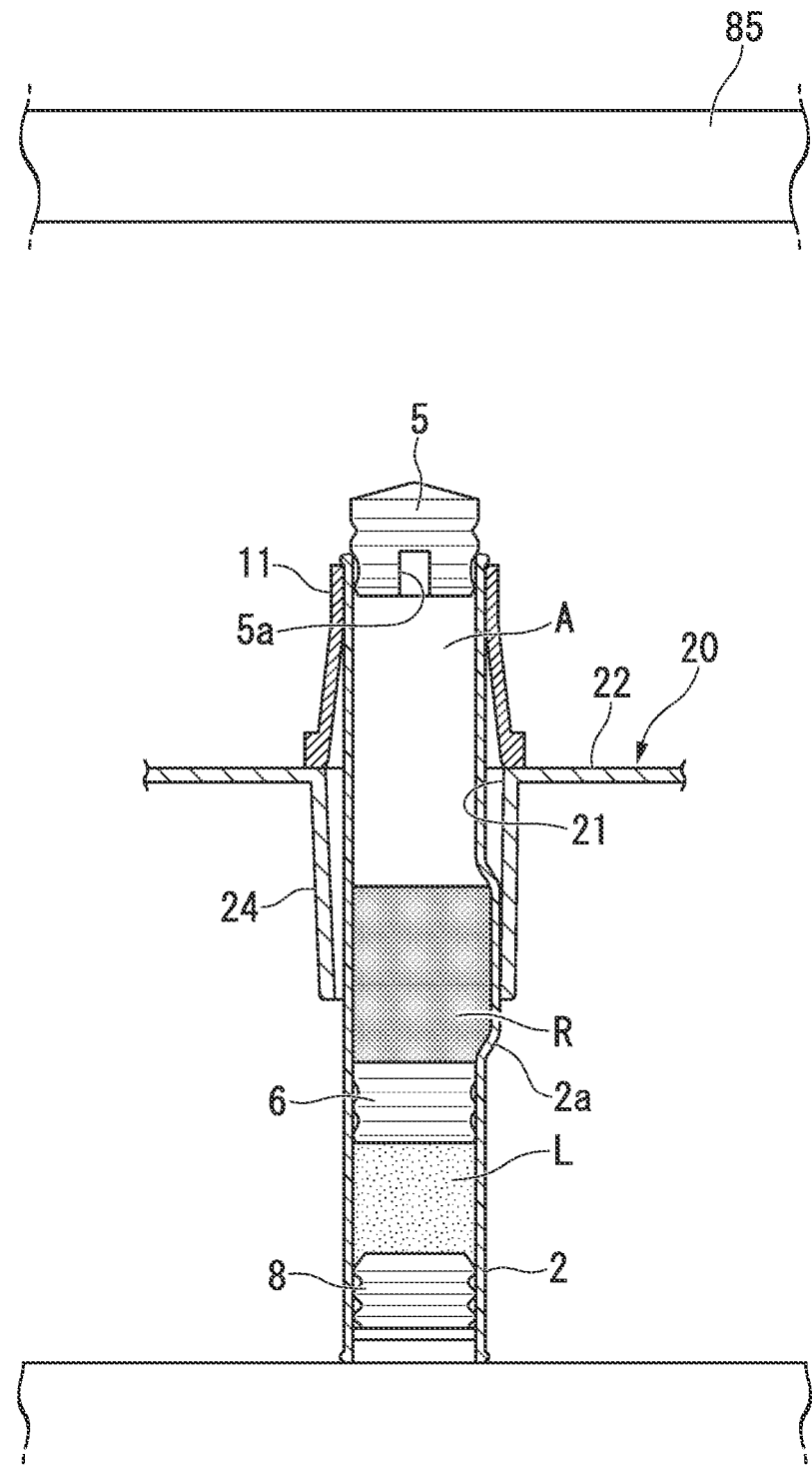
FIG. 16 is a drawing illustrating a state where the lyophilized preparation is obtained.

Then, as shown in FIG. 16, with increasing the vacuum degree, the moisture of the lyophilization solution R is released to the outside via the upper end of the cartridge 2 which is in a half-plugged state by the sublimation. This state is left as it is for a while, and thus the lyophilization of the lyophilization solution R proceeds and the lyophilization solution R is changed to a lyophilized preparation S by the sublimation.

After that, the inside of the freeze dryer is substituted with pure nitrogen gas until the pressure reaches to a predetermined pressure level. Accordingly, the moisture in the freeze dryer is removed, and at the same time, a descending position of the front stopper 5 is determined by the filling volume of the pure nitrogen gas and a space between the descending position and a lyophilization drug is determined in the internal space of the cartridge 2.

Figure 17:
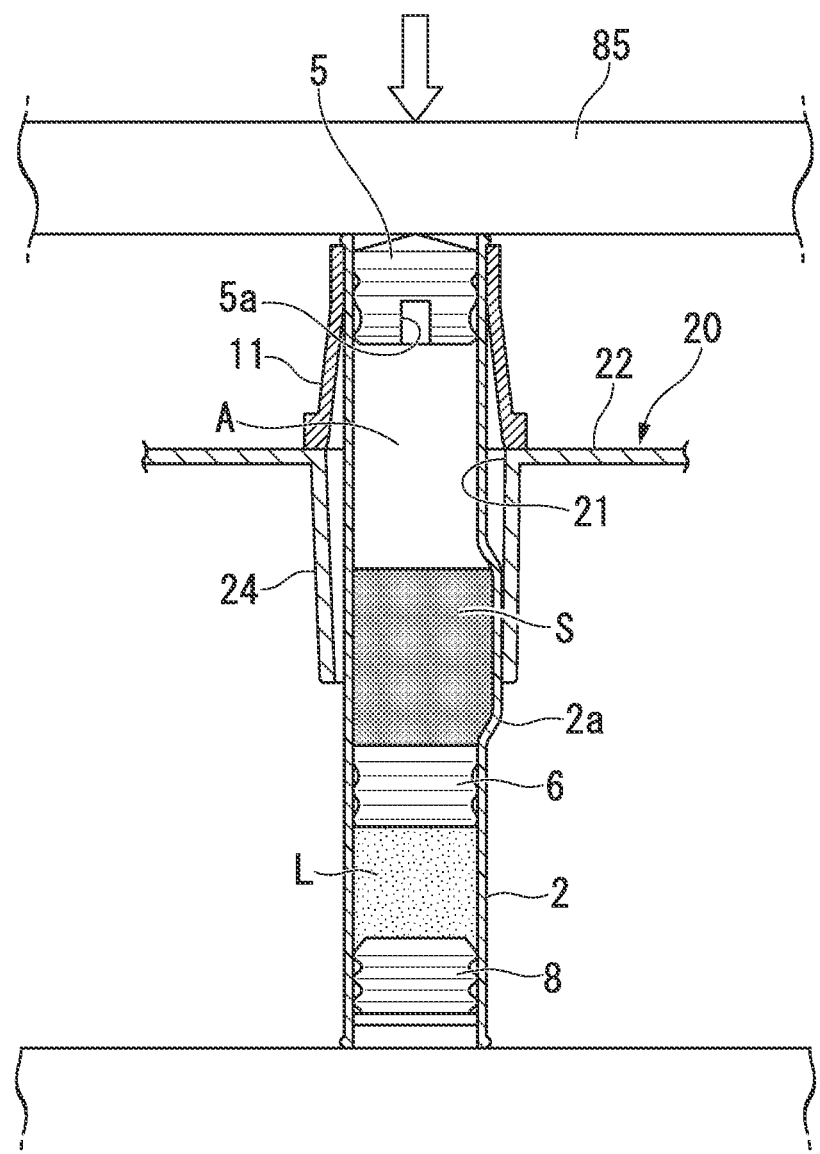
FIG. 17 is a drawing illustrating a state where the front stopper is pushed.
Figure 18:
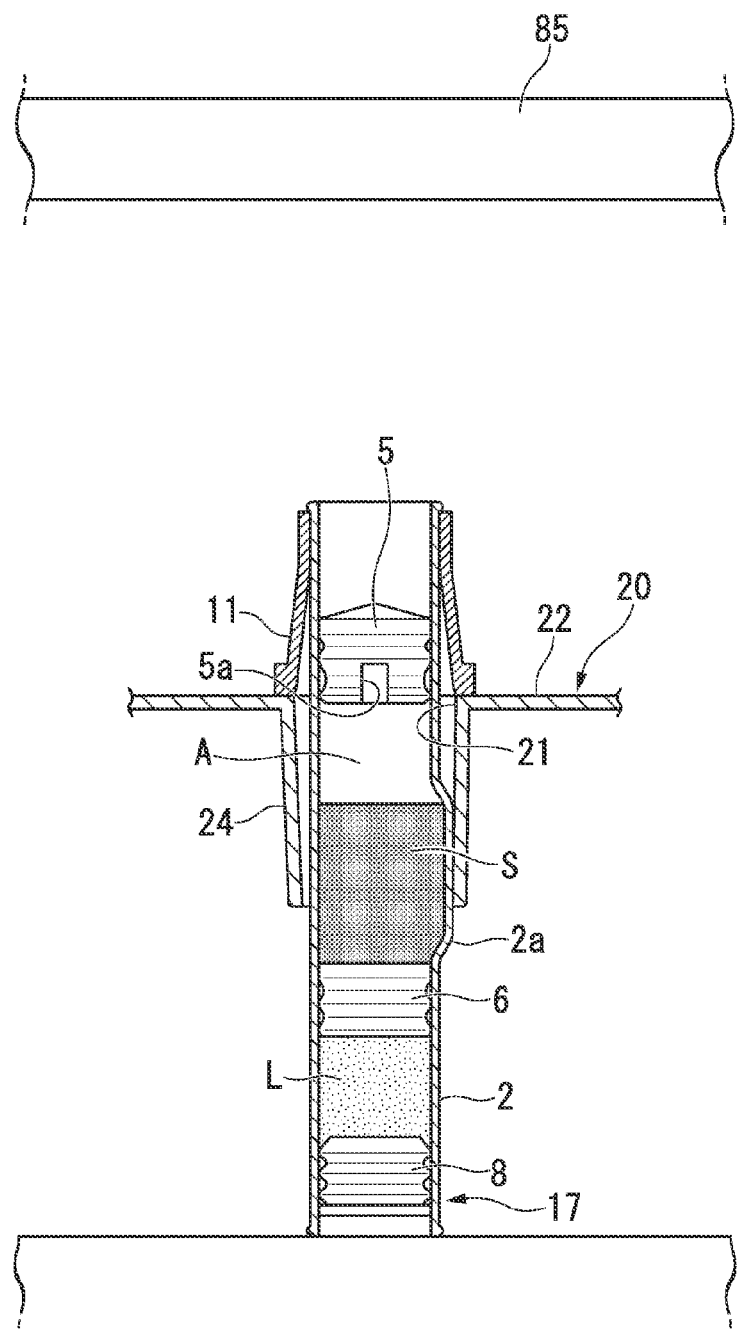
FIG. 18 is a drawing illustrating a state where the front stopper is moved downward.

Subsequently, the front stopper pushing processing S53 is performed. Here, as shown in FIG. 17, a shelf board 85 disposed on the upper part of the cartridge 2 in the freeze dryer moves downward while maintaining the horizontal condition. Accordingly, each shelf board 85 abuts the front stopper 5 in the plurality of cartridges 2, and the front stopper 5 is pushed into the cartridge 2. In this manner, the front stopper 5 pushed into the cartridge 2 moves downward by the pressure difference of the inside and the outside of the cartridge 2, and finally, according to the injection volume of the nitrogen gas, as shown in FIG. 18, the front stopper 5 is positioned at an appropriate position as a disposing position of the front stopper 5. Accordingly, a lyophilized preparation-filled cartridge 17 is formed.

Figure 19:
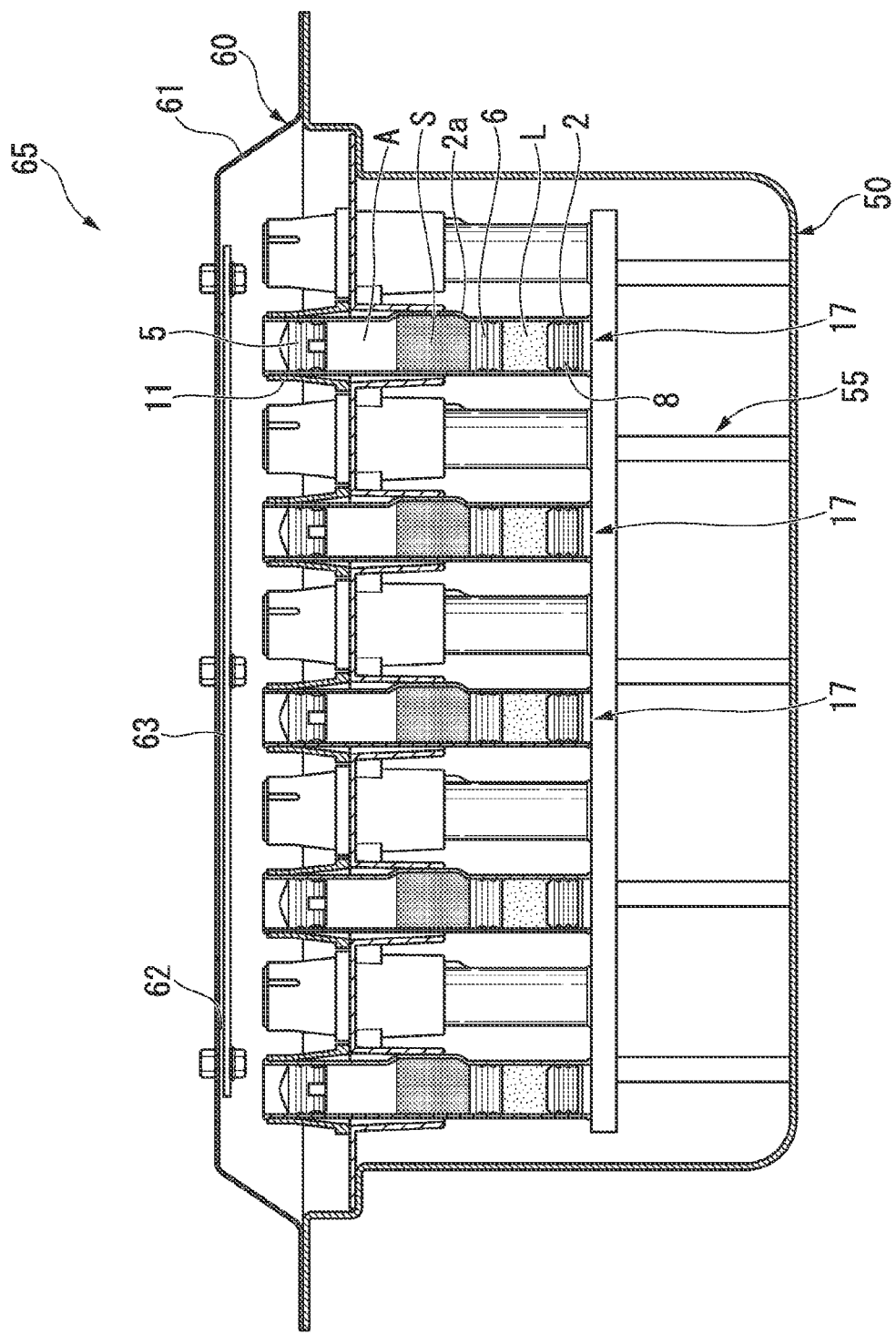
FIG. 19 is a longitudinal sectional view of the cartridge stowage container stowing the lyophilized preparation-filled cartridge after a lyophilization process.

The lyophilized preparation-filled cartridge 17 formed in such a manner is unpacked together with the steel tub 50 from the freeze dryer, and the lid member 60 is reattached to the lyophilized preparation-filled cartridge 17, as shown in FIG. 19.

The lyophilized preparation-filled cartridge 17 is kept standby in above condition until being carried to the next assembly process S6. In addition, since the lyophilized preparation-filled cartridge 17 is stowed in the cartridge stowage container 65 made of the steel tub 50 and the lid member 60, the sterility of the inner portion of the lyophilized preparation-filled cartridge 17 is ensured even during this standby time.

Then, the assembly process S6 is performed. In the assembly process S6, a front assembly (not shown) is attached to the lyophilized preparation-filled cartridge 17 unpacked from the nest 20 together with the holder 11, and when attaching the front assembly, the holder 11 is detached from the cartridge 2. After that, the combined container-syringe is completed by attaching the finger grip to the cartridge 2.

According to the above-described manufacturing method of the combined container-syringe, since the dissolving solution L can be filled in the bubble-free state in the vacuum plugging process S2, it is possible to prevent the end stopper 8 and the middle stopper 6 from moving even when the dissolving solution-filled cartridge 15 is heated in the steam sterilization process S3.

In other words, since the dissolving solution L is vacuum-filled, it is possible to easily perform the steam sterilization even after the cartridge 2 is filled with the dissolving solution L. Accordingly, it is possible to surely perform the sterilization of the dissolving solution L.

In addition, even when the pressure is reduced in the lyophilization process S5, since the air bubbles in the dissolving solution L do not expand, similarly to the above description, it is possible to prevent the end stopper 8 and the middle stopper 6 from moving.

Furthermore, the cooling deformation or the decompression deformation of the tub does not occur even in the steam sterilization process S3 and the lyophilization process S5 by using the steel tub 50 made of stainless steel. For this reason, through a series of processes, the tub can have a function as a tub which retains the cartridge 2 and the nest 20.

In addition, a diameter-reducing portion at which the diameter is reduced by one step from the inner peripheral surface may be formed on the rear end (lower end) in the inner peripheral surface of the cartridge 2. In this case, it is possible to prevent the end stopper 8 from protruding from the rear end side of the cartridge 2. In other words, since the diameter-reducing portion regulates the movement of the end stopper 8 toward the rear end side, for example, even when the air bubbles are slightly remain in the dissolving solution L, it is possible to prevent the end stopper 8 from moving caused by expanding the air bubbles during the steam sterilization and the lyophilization.

Figure 20:
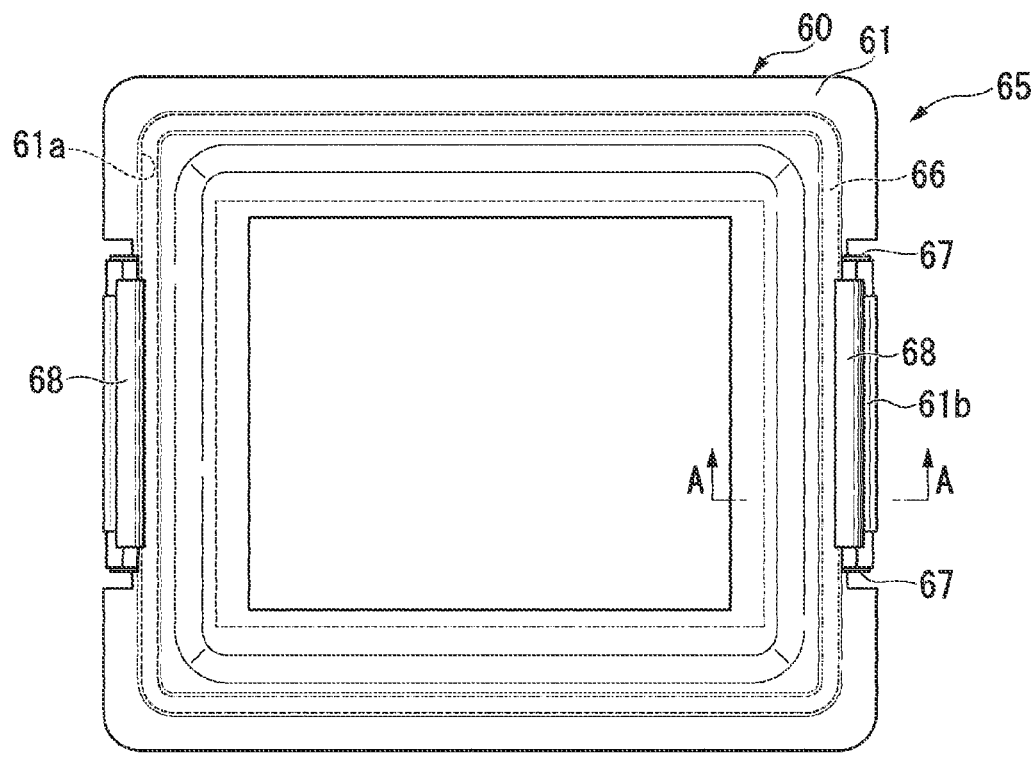
FIG. 20 is a plan view of the cartridge stowage container according to a modification example.
Figure 21:
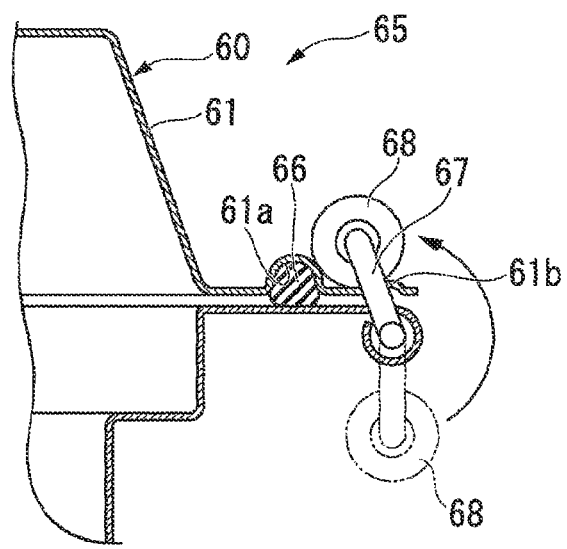
FIG. 21 is a cross-sectional view taken along the line A-A in FIG. 20.

In addition, the configuration shown in FIGS. 20 and 21, for example, may be modification examples of the cartridge stowage container 65.

In the cartridge accommodation container 65 of the modification example, a sealing member stowage portion 61a of which the lower surface is formed to be recessed upward in the outer peripheral portion of the lid main body 61 in the lid member 60, is formed to extend across the entire periphery. At a space between the lid main body 61 and the steel tub 50, there is provided a rubber sealing member 66 that extends across the entire periphery of the lid main body 61 along the sealing member stowage portion 61a stowed in the sealing member stowage portion 61a in the lid main body 61. The rubber sealing member 66 is formed of, for example, a silicone rubber or the like, and is adhered to the steel tub 50 across the entire periphery in a state where the rubber sealing member 66 is stowed in the sealing member stowage portion 61a.

Furthermore, among four sides on the outer periphery of the steel tub 50, on two sides that face each other, there is provided a roller 68 which is fixed to an arm 67 that is rotationally and movably attached around the axis line along these sides and to a distal end of the arm 67.

The roller 68 is in a state where the lid member 60 is not fixed in a state where the roller 68 is positioned in the lower part of the lid member 60. As the roller 68 rotationally moves on the upper part of the lid member 60, the roller 68 climbs over a protruded portion 61b provided at an outermost periphery of the lid main body 61 of the lid member 60 and is fixed to the upper surface of the lid member 60. Accordingly, the lid member 60 is integrally fixed to the steel tub 50, that is, the lid member 60 becomes a fixed condition.

As the roller 68 makes the lid member 60 be in a fixed condition in this manner, the rubber sealing member 66 between the lid member 60 and the steel tub 50 is compressed, and thus an inner space of the cartridge stowage container 65 defined by the lid member 60 and the steel tub 50 is air-tightly isolated from outside. Therefore, it is possible to ensure the sterility of the inner space of the cartridge stowage container 65 in a simple manner. In addition, as the roller 68 rotationally moves downward, it is possible to easily detach the lid member 60 from the cartridge.

While preferred embodiments of the present invention have been described and illustrated above, it should be understood that these are exemplary of the present invention and are not to be considered as limiting. Additions, omissions, substitutions, and other modifications can be made without departing from the spirit or scope of the present invention. Accordingly, the present invention is not to be considered as being limited by the foregoing description, and is only limited by the scope of the appended claims.

What is claimed is:

1. A manufacturing method of two-chamber type combined container-syringe, comprising:
    a dissolving solution filling process of preparing a dissolving solution-filled cartridge by inserting an end stopper into an inner side of a cartridge which extends along an axis line and has a cylindrical shape, filling a dissolving solution onto the end stopper inside the cartridge, and inserting a middle stopper into a bypass portion positioned on an upper part of the dissolving solution in the cartridge so that the bypass portion is in a communication state;
    a vacuum plugging process of eliminating air bubbles from the dissolving solution in the dissolving solution-filled cartridge and sealing the dissolving solution with the middle stopper after the dissolving solution filling process, and
    a steam sterilization process of sterilizing the dissolving solution-filled cartridge after the vacuum plugging process,
    wherein the vacuum plugging process includes
    a first cooling processing of cooling the inside of a vacuum plugging equipment in which the dissolving solution-filled cartridge is disposed to a cooling temperature at which the dissolving solution is not frozen,
    a first decompression processing of decreasing pressure inside the vacuum plugging equipment while the vacuum plugging equipment maintains the cooling temperature after the first cooling processing, and
    a middle stopper pushing processing of pushing the middle stopper downward and bringing the middle stopper into contact with the dissolving solution after the first decompression processing,
    wherein the steam sterilization process is performed in a state where a plurality of cartridges are stowed inside a steel tub which is formed of stainless steel, an upper part of which is open, and which has a box shape, is disposed at an angle such that the axis line of the cartridge is inclined relative to a vertical direction.

2. The manufacturing method of two-chamber type combined container-syringe according to claim 1,
    wherein the cooling temperature is 0 to 10 C in the first cooling processing, and
    wherein the pressure inside the vacuum plugging equipment is reduced to a pressure in the range of 5 to 15 mbar in the first decompression processing.

3. The manufacturing method of two-chamber type combined container-syringe according to claim 1,
    wherein the vacuum plugging process further includes an index temperature measurement processing of measuring the temperature of the dissolving solution in a cooling index cartridge with the same configuration as the dissolving solution-filled cartridge which is disposed in the vacuum plugging equipment and formed by the dissolving solution filling process, and
    wherein the first decompression processing is performed when the temperature of the dissolving solution in the cooling index cartridge becomes the cooling temperature after the first cooling processing.

4. The manufacturing method of two-chamber type combined container-syringe according to claim 2,
    wherein the vacuum plugging process further includes an index temperature measurement processing of measuring the temperature of the dissolving solution in a cooling index cartridge with the same configuration as the dissolving solution-filled cartridge which is disposed in the vacuum plugging equipment and formed by the dissolving solution filling process, and
    wherein the first decompression processing is performed when the temperature of the dissolving solution in the cooling index cartridge becomes the cooling temperature after the first cooling processing.

5. The manufacturing method of two-chamber type combined container-syringe according to claim 1, further comprising:
    a lyophilization solution filling process of preparing a lyophilization solution-filled cartridge in which the lyophilization solution is sealed together with internal gas by a front stopper and the middle stopper, by filling the lyophilization solution on the middle stopper which is inside the dissolving solution-filled cartridge after the steam sterilization process and by inserting the front stopper above the lyophilization solution in the cartridge; and
    a lyophilization process of forming a lyophilized preparation from lyophilization solution after the lyophilization solution filling process,
    wherein the lyophilization process includes
    a second cooling processing of cooling the temperature inside a freeze dryer in which the lyophilization solution-filled cartridge is disposed,
    a second decompression processing of making the front stopper be in a half-plugged state with respect to the cartridge by reducing the pressure inside the freeze dryer to be the pressure lower than that of the internal gas, while the temperature inside the freeze dryer is cooled after the second cooling processing, and
    a front stopper pushing processing of pushing the front stopper downward after changing the lyophilization solution to the lyophilized preparation by a sublimation by further reducing pressure in the freeze dryer after the second decompression processing.

6. The manufacturing method of two-chamber type combined container-syringe according to claim 5,
    wherein the dissolving solution filling process, the vacuum plugging process, the steam sterilization process, the lyophilization solution filling process, and the lyophilization process are performed in a state where the plurality of cartridges are horizontally aligned and supported in a nest.

7. The manufacturing method of two-chamber type combined container-syringe according to claim 6,
    wherein the vacuum plugging process, the steam sterilization process, and the lyophilization process are performed in a state where the plurality of cartridges are stowed together with the nest inside the Hall steel tub.

8. The manufacturing method of two-chamber type combined container-syringe according to claim 7,
wherein the steam sterilization process is performed in a state where the opening of the steel tub is closed with a lid main body made of stainless steel and with a lid member having a filter that closes a hole portion of the lid main body.

9. The manufacturing method of two-chamber type combined container-syringe according to claim 7,
wherein a spacer is provided which abuts both a bottom surface of an inner side of the steel tub and a lower end of the plurality of cartridges.

10. The manufacturing method of two-chamber type combined container-syringe according to claim 7,
wherein height positions of each upper end of the plurality of cartridges stowed in the steel tub become the same and are positioned higher than the opening edge portion of the steel tub, and
wherein the front stopper pushing processing is performed by making a shelf board horizontally extended abuts the front stopper which is in a half-plugged state with respect to each cartridge from above.

* * * * *